US012340377B2

(12) United States Patent
Ammatanda et al.

(10) Patent No.: US 12,340,377 B2
(45) Date of Patent: Jun. 24, 2025

(54) CARD PRESENT PAYMENT DEDUPLICATION

(71) Applicant: Hint, Inc., Pleasanton, CA (US)

(72) Inventors: Muthanna Nischal Ammatanda, Fremont, CA (US); Ram Prasad Gotru, Mountain House, CA (US); Rhys Andersson Lee Chiu, Daly City, CA (US)

(73) Assignee: Hint, Inc., Pleasanton, CA (US)

( * ) Notice: Subject to any disclaimer, the term of this patent is extended or adjusted under 35 U.S.C. 154(b) by 231 days.

(21) Appl. No.: 18/362,448

(22) Filed: Jul. 31, 2023

(65) Prior Publication Data
US 2025/0045767 A1 Feb. 6, 2025

(51) Int. Cl.
| G06Q 40/00 | (2023.01) |
| G06N 5/022 | (2023.01) |
| G06Q 20/02 | (2012.01) |
| G06Q 20/20 | (2012.01) |
| G06Q 20/40 | (2012.01) |
| G16H 40/20 | (2018.01) |

(52) U.S. Cl.
CPC .......... *G06Q 20/407* (2013.01); *G06N 5/022* (2013.01); *G06Q 20/027* (2013.01); *G06Q 20/202* (2013.01); *G06Q 20/204* (2013.01); *G16H 40/20* (2018.01)

(58) Field of Classification Search
None
See application file for complete search history.

(56) References Cited

U.S. PATENT DOCUMENTS

| 10,354,239 B1* | 7/2019 | Nguyen | G06Q 30/0641 |
| 11,488,173 B1* | 11/2022 | Wall | G06Q 20/20 |
| 2005/0182780 A1* | 8/2005 | Forman | G06F 16/215 |
| 2006/0259438 A1* | 11/2006 | Randle | H04L 63/20 |
| | | | 705/65 |
| 2015/0081462 A1* | 3/2015 | Ozvat | G06Q 20/40 |
| | | | 705/21 |
| 2017/0337532 A1* | 11/2017 | Choi | H04L 51/046 |
| 2021/0365935 A1* | 11/2021 | Tripathy | G06F 11/079 |
| 2022/0188805 A1* | 6/2022 | Debellis | G06Q 20/065 |

FOREIGN PATENT DOCUMENTS

KR 20190159585 A * 6/2021 .......... G06Q 20/407

* cited by examiner

*Primary Examiner* — Olabode Akintola
(74) *Attorney, Agent, or Firm* — Ballard Spahr LLP

(57) ABSTRACT

A payment processing system can detect an attempted re-initiation of a payment transaction for the same purchase of an item or service. In some examples, the system compares initial transaction data against re-initiated transaction data to identify the attempted duplicated payment. Based on the identified attempted duplicated payment, initiating a payment deduplication phase by generating a potential payment duplication alert for presentation at the POS terminal device and/or in the user interface of a mobile device.

24 Claims, 21 Drawing Sheets

CARD PRESENT PAYMENT DEDUPLICATION

TECHNICAL FIELD

Embodiments herein generally relate to card present payment deduplication. More specifically, but not by way of limitation, embodiments relate to systems, methods and media for issuing a user alert when a potential duplicate payment is detected.

BACKGROUND

Conventional payment systems that process credit card payments typically issue an alert when a payment is "declined" due to insufficient funds, for example. No other information about the payment failure is provided. A user might try the payment again using another source of funds in the hope the payment goes through. Occasionally, a payment might go though twice. This uncertainty, lack of information, and potential payment duplication is not helpful to the payer, or a shop assistant or staff member helping the payer to pay for a product or service, for example.

BRIEF SUMMARY

Some examples herein generate an alert based on a detection that multiple payments are being issued for the same purchase, in order to prevent multiple payments being collected for the same purchase. Examples seek to provide a technical solution assisting users to prevent re-running multiple payments for the same purchase, either inadvertently or due to system glitches.

DETAILED DESCRIPTION

Figure 1:
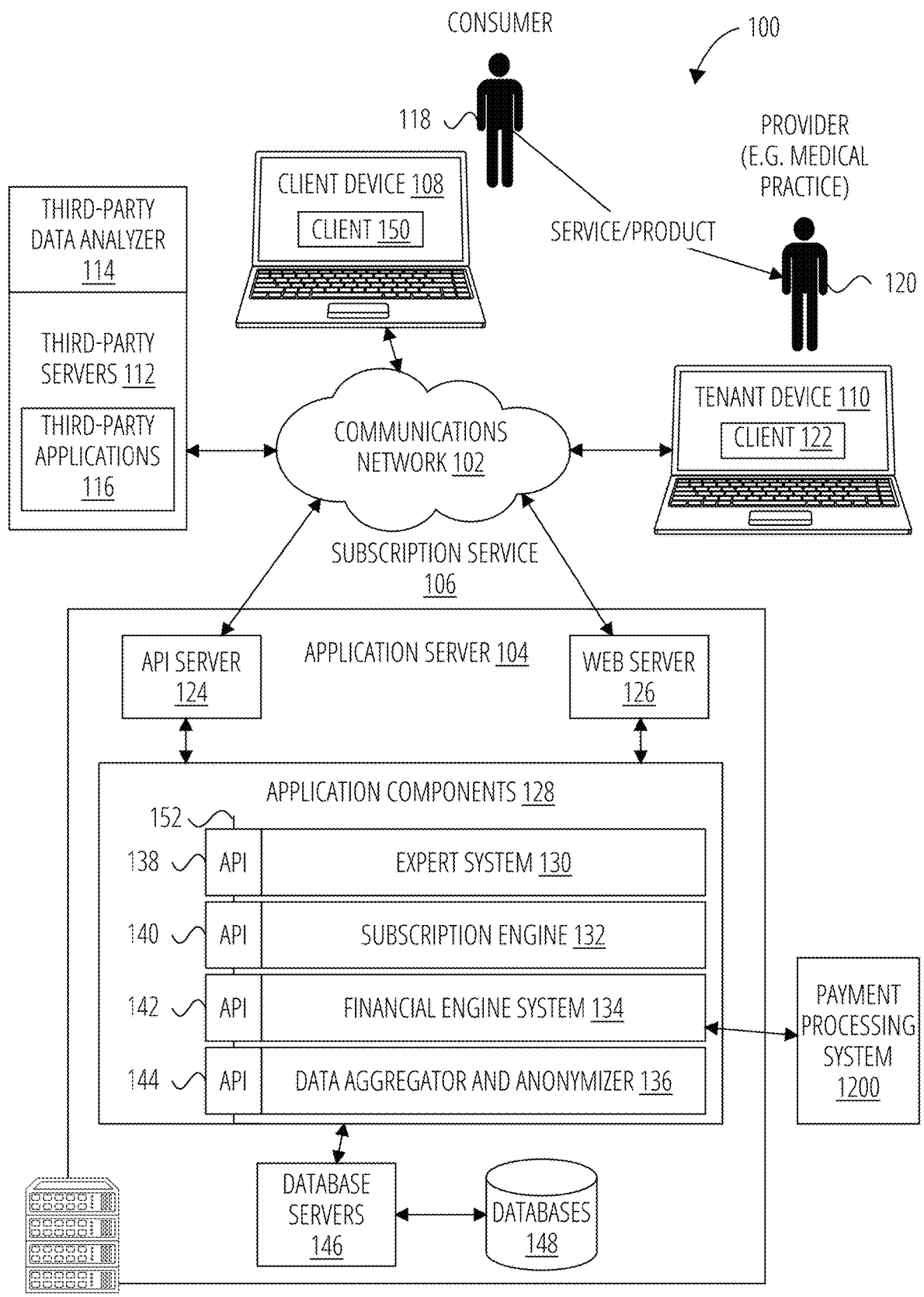
FIG. 1 illustrates a networked multi-tenant network in which the described technology, according to some example embodiments, may be deployed.

According to some example embodiments, there is provided a subscription management system that generates and uses data structures and interfaces that allow for configurability and flexibility in the creation of a bundle of subscriptions, for a specific consumer, to one or more products or services, which may be delivered in terms of one or more plans. Payment for the bundle of subscriptions, products or services may be made using a "card present" transaction. Sometimes these payments can fail due to system failure, or insufficient source funds for example. A paying user might try the payment again using another source of funds in the hope the payment goes through. Occasionally, a payment might go though twice. As mentioned above, this uncertainty, lack of information, and potential payment duplication is not helpful to the user, or a shop assistant or staff member helping the payer to pay for the bundle, product or service. Some examples herein generate an alert based on a detection that multiple payments are being issued for the same purchase, in order to prevent multiple payments being collected for the same purchase. Examples seek to provide a technical solution assisting users to prevent re-running multiple payments for the same purchase, either inadvertently or due to system glitches.

Each subscription within a bundle of subscriptions can be for a product or service and has a fulfillment price. Further, each subscription has a period in which it may recur (e.g., one month, six months, one year, etc.). These recurrence periods may perpetuate indefinitely or may terminate after a set number of occurrences (or cycles).

Each subscription can furthermore be financed by a loan from a third party, or by a service provider. Alternatively, a consumer can pay the full amount for a subscription at one time (e.g., upon initiation of the subscription). The terms of the subscription (both delivery and financial) can be dynamically managed by consumers in some cases (e.g., a consumer may be able to change the time period over which the subscription may recur).

Even further, each subscription may be executed independently of other subscriptions in a bundle, while billing for one or more subscriptions within the bundle may be aggregated into a single payment once a month (or on some other periodic basis). Service plans may, in some embodiments, be made with the assistance of a service delivery expert (e.g., a physician), and may be fulfilled at a place of business of the expert (e.g., a medical practice office of the physician). Product fulfillment, on the other hand, may be performed by shipment.

As noted above, each subscription in a bundle may be financed by a loan from a third party or service provider. In one embodiment, loans may be facilitated in real time. To this end, a subscription engine communicates details of a particular subscription to a financial exchange in near real-time. The details of a particular description include, for example, identification of the products or services being offered, details of the provider, and details of the consumer. Third-party financiers may access the financial exchange, again in near real-time, to accept any number (or none) of the subscriptions being offered via the financial exchange.

In one embodiment, the receipt of subscription details, the offering of subscription financing opportunities to third-party financiers, and the receipt of acceptance/decline of a financing opportunity may occur in near real-time, and while a customer is standing at the checkout counter of a service consumer.

Defining the quantity and frequency of delivery of a product or service offering under subscription plan is tricky and presents technical challenges to a user. This is particularly so where the product or service offering is being subscribed to is part of a bundle of offerings or services included within a single subscription plan. For example, defining the quantity and frequency of delivery requires typing numerical data into appropriate fields and then calculating variables to display a monthly cost (or payment total) of the subscription plan. Because this area of the software is frequently used on a touchscreen tablet device while the customer is watching, now there is a need to have a fast friction free device to enter the data.

NOTE In some further examples, [insert consistory clauses].

FIG. 1 illustrates a networked multi-tenant network 100 in which a communications network 102 communicatively couples application servers 104 at a subscription service 106, a user device 108, a POS terminal device 110, and third-party servers 112. The third-party servers 112 may be accessed and operated by a third-party data analyzer 114 (e.g., a "big data" company), for example. The third-party servers 112 host third-party applications 116.

The user device 108 is accessed by a user 118 and processes operations and applications (e.g., a browser application, or commercial platform) sourced from or associated with a tenant 120. The tenant 120 may include a medical practice or service provider operating in a group of networked practices, for example. The user 118 may be a patient of the medical practice, for example. The POS terminal device 110 is accessed and operated by the tenant 120 to host and process tenant operations and tenant applications 122. In some examples, the multi-tenant network includes a great multiplicity of tenants 120, each communicatively coupled with the subscription service 106.

The application servers 104 include an API server 124 and a web server 126 which, in turn, facilitate access to several application components 128 that include an expert system 130, a subscription engine 132, a financial engine system 134, and a data aggregator and anonymizer 136. Each of these components is provided with a respective API, namely an API 138, an API 140, an API 142, and an API 144.

The application components 128 are communicatively coupled to database servers 146 which in turn facilitate access to one or more databases 148.

In an example scenario, a tenant 120 (e.g., a medical practice) may wish to provide offerings (e.g., products or services) to a user 118 (e.g., a patient), either as a once-off/one-time delivery or as part of a subscription plan which has a recurrence. In this example, the medical practice, i.e., tenant 120, may also wish to provide the patient, i.e., user 118 with the option of paying for a health product or consultation as a once-off payment, as a subscription payment, or as a combination of a once off payment and a subscription payment.

At a high level, the expert system 130 operates to enable an expert in a particular vertical (e.g., the medical practice or tenant 120) to define and manage a plan for the delivery of various products and services to its patients or users 118. An expert system 130 is accordingly specifically constructed and programmed for the creation of a plan for the delivery of a specific product or service in a particular product or service vertical.

The subscription engine 132 is responsible for the automated management of a plan (which may or may not include any number of subscriptions to products or services).

The financial engine system 134 is responsible for communicating financing opportunities related to a plan to one or more financiers (e.g., who may operate as a provider, or who may be a third party accessing the financial engine system 134 via the third-party applications 116).

In some examples, the financial engine system 134 may include or be connected to a payment processing system 1200 discussed further below in relation to FIG. 12. The payment processing system 1200 is responsible for operations relating to card present payment deduplication. More specifically, but not by way of limitation, some examples include systems, methods and media for issuing a user alert when a potential duplicate payment is detected.

Some examples herein generate an alert based on a detection that multiple payments are being issued for the same purchase in order to prevent multiple payments being collected for the same purchase. Examples thus seek to provide a technical solution assisting users to prevent re-running multiple payments for the same purchase, either inadvertently or due to system glitches.

Figure 2:
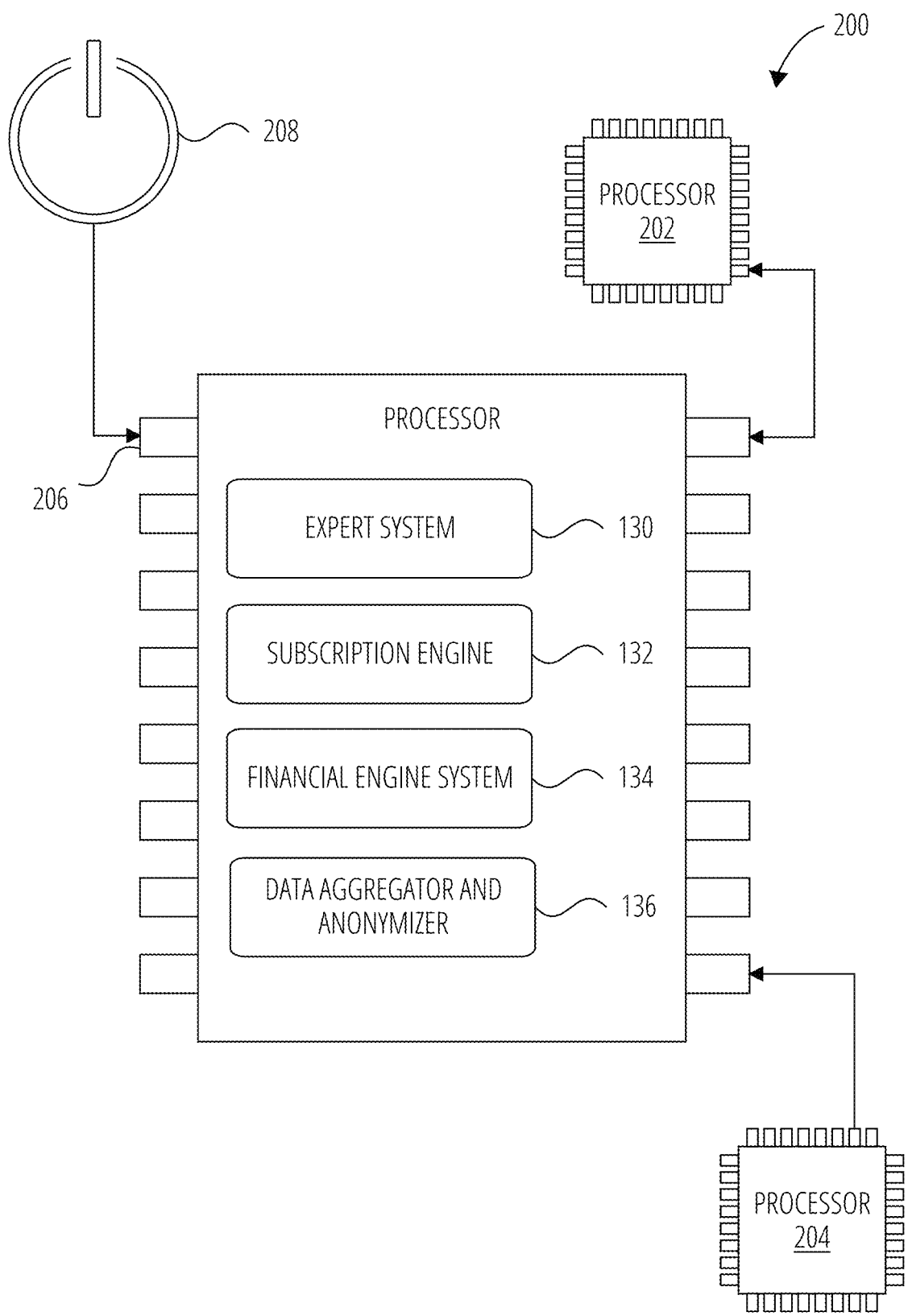
FIG. 2 is a diagrammatic representation of a processing environment, in accordance with one embodiment.

FIG. 2 is a diagrammatic representation of a processing environment 200, which includes a processor 202, a processor 204, and a processor 206 (e.g., a GPU, CPU, or combination thereof). The processor 206 is shown to be coupled to a power source 208, and to include (either permanently configured or temporarily instantiated) modules, namely the expert system 130, the subscription engine 132, the financial engine system 134, and the data aggregator and anonymizer 136. The expert system 130 operationally supports a guided process for the selection of products or services, as well as the attributes of such products and services (e.g., quantity (units), a frequency of delivery and number of deliveries), to include in a subscription.

The subscription engine 132 operationally calculates and presents information relating to overall options related to a subscription for bundled purchase, and the financial engine system 134 operationally allows third parties (e.g., lenders) to view financing opportunities and accept or reject such financing opportunities for subscriptions (or bundles of subscriptions) generated by the subscription engine 132.

As illustrated, the processor 206 is communicatively coupled to both the processor 202 and processor 204 and receives data from the processor 202, as well as data from the processor 204. Each of the processor 206, processor 202, and processor 204 may host one or more of an expert system 130, a subscription engine 132, a financial engine system 134, and a data aggregator and anonymizer 136.

Figure 3:
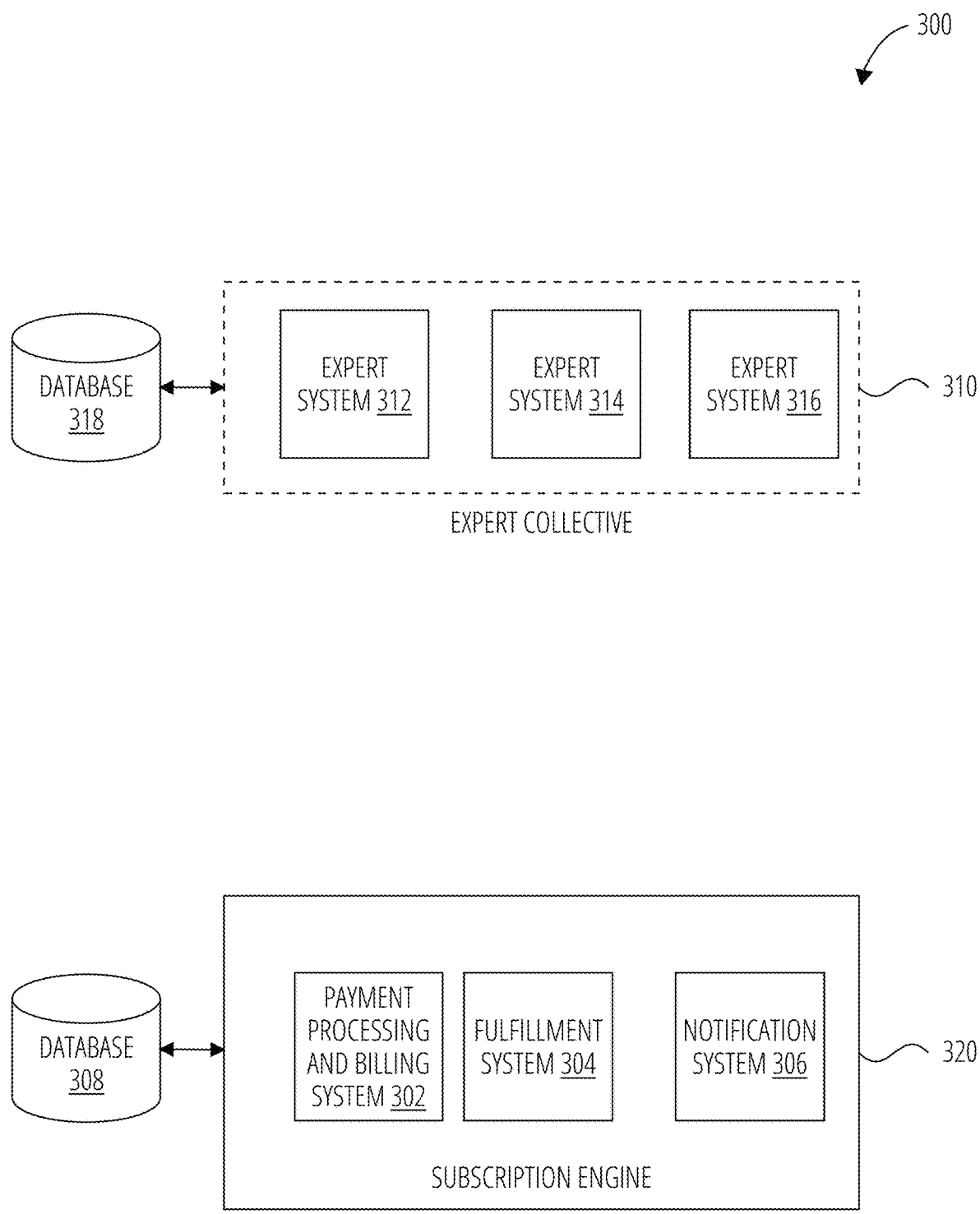
FIG. 3 illustrates further details regarding the subcomponents of a subscription engine, according to some example embodiments.

FIG. 3 illustrates the various sub-components of a subscription engine 320, namely a payment processing and billing system 302, a fulfillment system 304, and a notification system 306. The payment processing and billing system 302 is operationally responsible for the processing of payments and issuing of invoices/bills. The fulfillment system 304 communicates with third parties for the shipping of goods, when appropriate, as well as with service providers to record the delivery of goods and services to a customer. The notification system 306 operationally provides notifications to both customers and service providers regarding upcoming fulfillment events, as well as other delivery-related events.

The subscription engine 320 is also communicatively coupled to a database 308, to both store and retrieve data needed by each of the payment processing and billing system 302, the fulfillment system 304 and the notification system 306. The fulfillment system 304 creates and tracks the fulfillment or delivery of a service or a product. For example, for a service, the fulfillment system 304 records what was rendered or provided (e.g., what, how much, when, value) and uses the notification system 306 to remind users of appointments for a follow-up service. For products, the fulfillment system 304 issues orders, tracks shipping and delivery, in addition to tracking what was rendered and provided.

The notification system 306 is a messaging system that uses different media or messaging channels (e.g., email, text, push notification, etc.) to alert customers, providers (e.g., practices) and operations of different events.

FIG. 3 also illustrates that a subscription system may include an expert collective 310 comprising respective and distinct expert systems, namely an expert system 312, an expert system 314 and an expert system 316. Each of the expert systems may be dedicated to a specific vertical and provide a guided process for the creation of subscription and plans for customers in that vertical. For example, the expert system 312 may be dedicated to a cosmetics and beauty care vertical, the expert system 314 may be dedicated to a bicycle service vertical, and the expert system 316 may be dedicated to a car service vertical. Each of the expert systems within the expert collective 310 may furthermore communicatively coupled, and have access to, a respective database 318.

Figure 4:
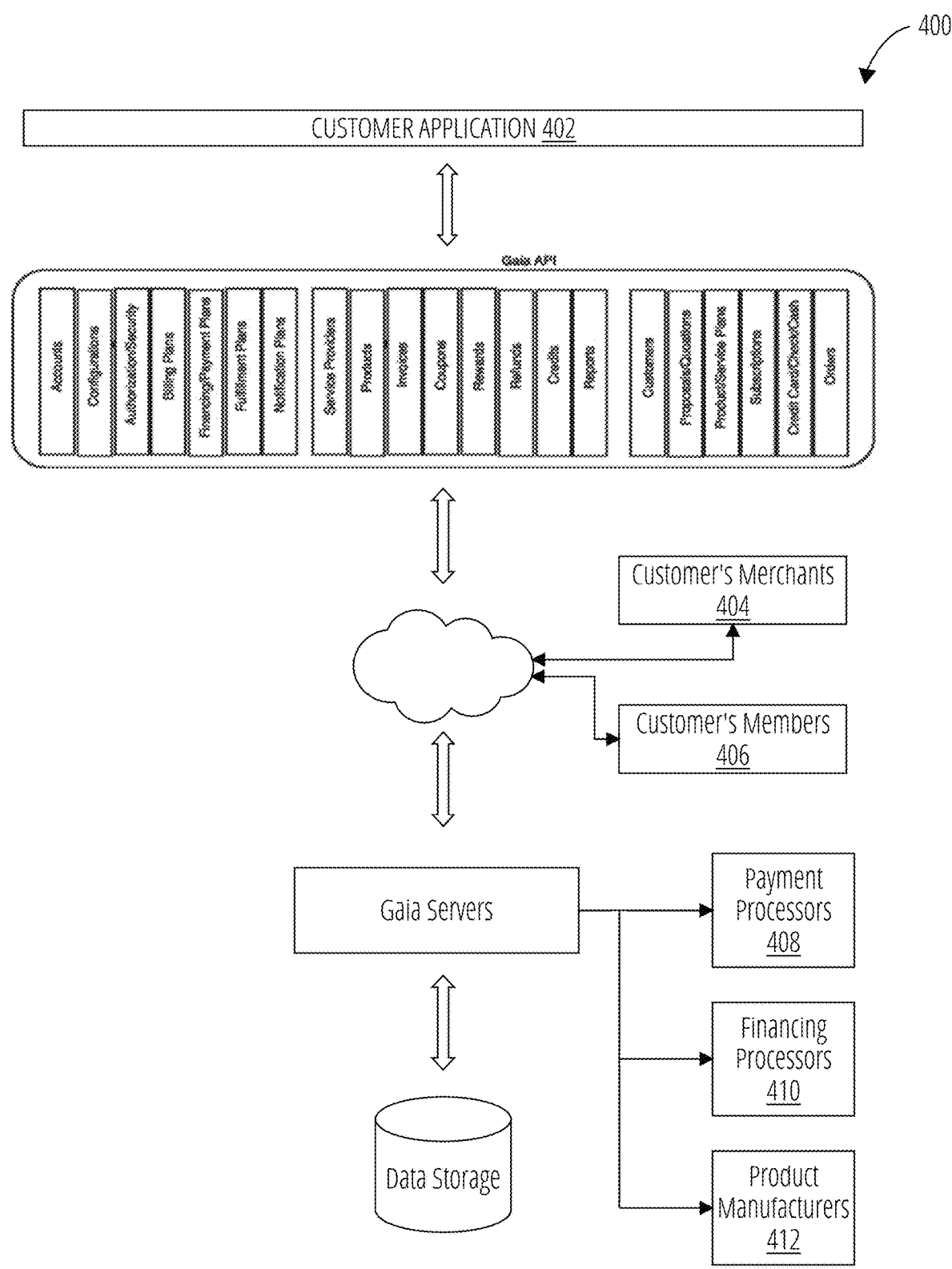
FIG. 4 is a block diagram illustrating further architectural details of a subscription system, according to some example embodiments.

FIG. 4 is a block diagram illustrating a subscription management system 400 and shows further details for a specific example embodiment. The subscription management system 400 includes a customer application 402 that, via the API server 124 and the communications network 102, accesses the application component 128. The API server 124 is shown to support many functions provided by the application component 128, using data store to and retrieved from the database 148.

The customer application 402, via the API server 124 and the communications network 102, is also able to access customer's merchant 404 and customer's member 406. The application component 128 is also shown to exchange information and data with payment processors 408, financing processors 410 and product manufacturers 412.

The subscription management system 400 is, in one example embodiment, a cloud-based e-commerce solution built for developers to streamline and shorten the time to market of any e-commerce system that implements a variety of subscription models, quotations, recurring billings, electronic payments, order financing, order fulfillment, loyalty program, and notifications. The subscription management system 400 provides a rich set application programming interface (API) for developers to seamlessly integrate with their own systems. Modules and their APIs that developers can use to customize the subscription management system 400 to meet their own needs are as follows:

Accounts: primary account management and authorization.
Billing Plans: billing plan cycle options.
Financing/Payment Plans: members payments and financing options.
Fulfillment Plans: order fulfillment process.
Notification Plans: upcoming product/service notifications.
Service Providers: service providers information and configurations.
Products: products/services configuration.
Invoices: members' invoices and invoice line items.
Refunds: members' refunds management.
Credits: members' credits management.
Reports: analytical data on membership, financials, etc.
Coupons: coupons management.
Rewards: loyalty reward program for membership.
Customers: members management.
Product/service Plans: members' product/service plans management.
Proposals/Quotations: proposals and quotations.
Subscriptions: members' subscription configuration and management.
Credit Card/Check/Cash: member's credit card/check/and cash management.
Sample Data FlowRegister a business account with the subscription management system 400.
AccountResponse account=createAccount (AccountRequest request)Creates a treatment plan for members that all subscribed services are paid on the same date, the same invoice on a monthly basis.
BillingPlanResponse billingPlan=createBillingPlan(BillingPlanRequest request)Create a one-time payment plan for its subscribers.
PaymentPlanResponse paymentPlan=createPaymentPlan (PaymentPlanRequest request)Create a recurring payment plan for its subscribers. Request Ex: {"name: "Monthly Payment", payment_gateway: gateway_id, payment_count: 0, . . . });
Create some fulfillment plans (1 month, 2 month, . . . , 12 months) for providers to useFulfillmentPlanResponse fulfillmentPlan1=createFulfillmentPlan(FulfillmentPlanRequest request)
Create some notification plans for providers to use for any subscription's order.
NotificationPlanResponse notificationPlan1=createNotificationPlan(NotificationPlanRequest request)
Create a providerProviderResponse response=API.createProvider(new ProviderRequest( ))
Create coupons from own product catalog for its members.

CouponRequest couponRequest=new CouponRequest( )Create products for its members.
ProductResponse product=createProduct (ProductRequest request)
Registers a new memberCustomerResponse customerResponse=API.createCustomer (customerRequest);
Add CC to a member
CardResponse cardResponse=API.createCard (cardRequest); String cardId=cardResponse.apiData.card.getCardId ( );
Create a treatment plan for a member.
SubscriptionPlanResponse subscriptionPlanResponse=API.createSubscriptionPlan (subscriptionPlanRequest);
Create different subscriptions for a member.
SubscriptionResponse subscriptionResponse=API.createSubscription(subscriptionRequest);
Get pending Invoice of a subscription plan.
InvoiceResponse invoiceResponse=API.listInvoices(invoiceRequest); Charge a pending invoice of a subscription plan (Transaction)
TransactionResponse=API.chargeInvoice (transactionRequest);
Get member's upcoming order fulfillment under a subscription planorder list=list_order({"subscription_plan_id": "pla_9473c93", "filter": "pending"})
Updateexpert updates member's order fulfillment; i.e. confirmed, fulfilled, etc.status=update_order({"order_id": "or_9473c93", "status": "completed"}

Figure 5:
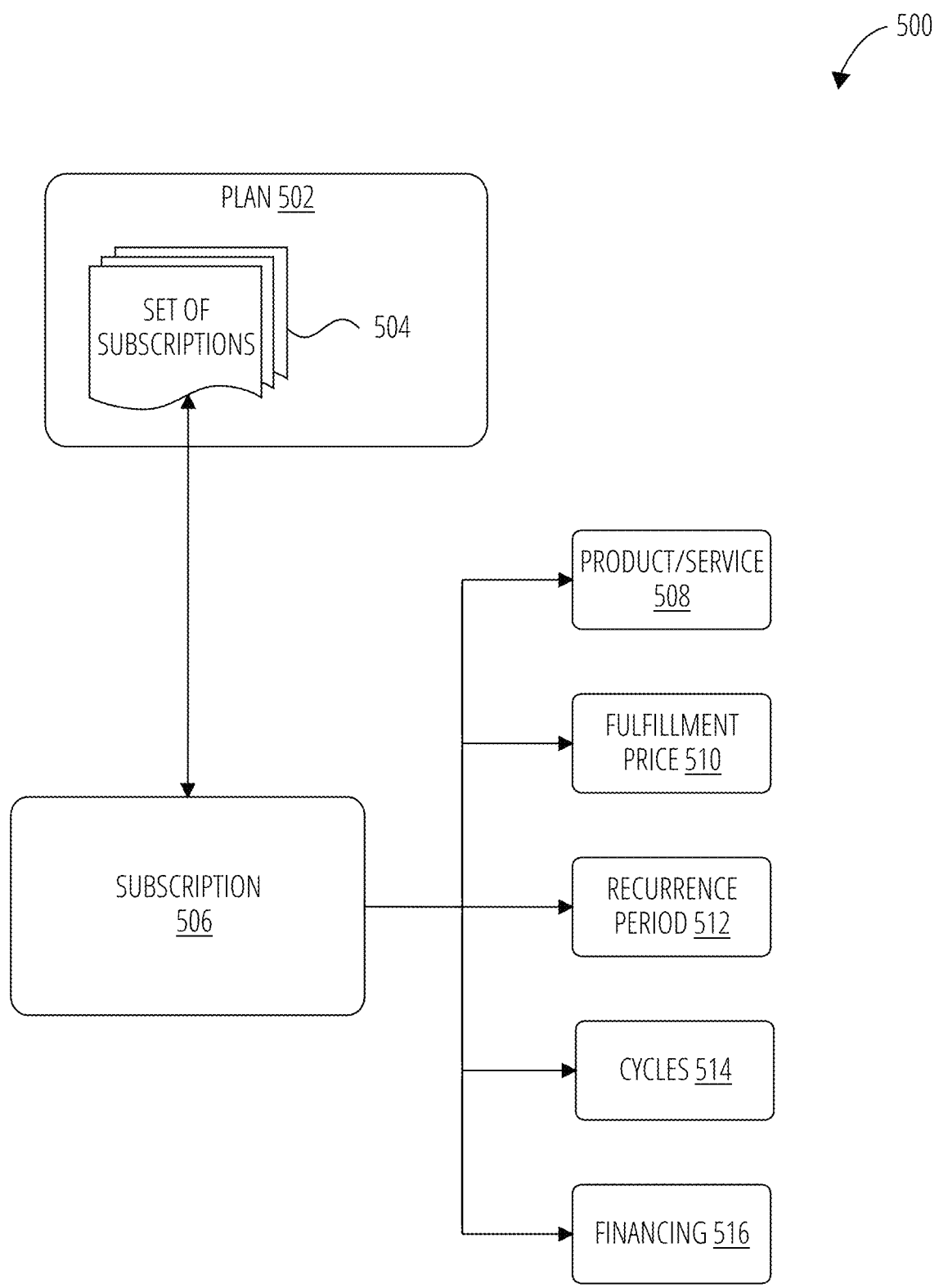
FIG. 5 is a diagrammatic representation of data structures maintained by a subscription service, according to some example embodiments.

FIG. 5 is a diagrammatic representation of a data architecture 500 created using and maintained by the subscription engine 320. A plan 502 includes a set of subscriptions 504. Each subscription 506 of the set of subscriptions 504 is for a product or service and has several attributes, a subset of which is shown in FIG. 5. Specifically, each subscription 506 relates to a specific product/service 508, has a fulfillment price 510, and a recurrence period 512. With respect to the recurrence period 512, a subscription 506 has some time period after which the subscription 506 recurs, e.g., must again be fulfilled. A subscription 506 may furthermore have a specified number of cycles 514 and may occur indefinitely or terminate after the specified number of the cycles 514.

A subscription 506 furthermore has associated financing 516. A subscription 506 may be financed via a loan or via a service provider directly as part of the service provider's subscription business. Alternatively, a subscription 506 may be fulfilled at the time of ordering.

Attributes of the subscription 506 may be managed by customers in some cases. For example, the cycles 514 may be modified or changed by a customer using the client 150 in order to interact with the subscription engine 320.

A specific subscription 506 may furthermore be executed independently of any other subscriptions included in a set of subscriptions 504, with the exception that billing is aggregated to a single payment at predetermined intervals (e.g., once a month).

A plan 502 for the delivery of service may be constructed or defined with the help of an expert (e.g., a physician or doctor) using an appropriate expert system 312, and performance/delivery of a subscription 506 of the plan 502 may be fulfilled at the expert's place of business (e.g., the doctors practice). A plan 502 for the delivery of a product may be fulfilled by shipment from a third party.

To facilitate financing (e.g., a loan as part of the financing 516) in near real-time, the subscription engine 320 is communicatively coupled to the financial engine system 134 to enable the subscription engine 320 digitally to communicate details about a particular subscription 506 or set of subscriptions 504 to the financial engine system 134. Financiers then access the financial engine system 134 (e.g., using a third-party application 116) to optionally accept a financing offer relating to a particular set of subscriptions 504 or subscription 506.

This facilitation of financing by a financier happens in near real-time as, in a typical scenario, a customer is physically present at the checkout counter of a service provider. To this end, the financial engine system 134 operationally aggregates accepted financing and rates, refusals and regular recurring subscriptions amounts to create a quote for a total monthly price for all subscriptions within a set of subscriptions 504.

Figure 6:
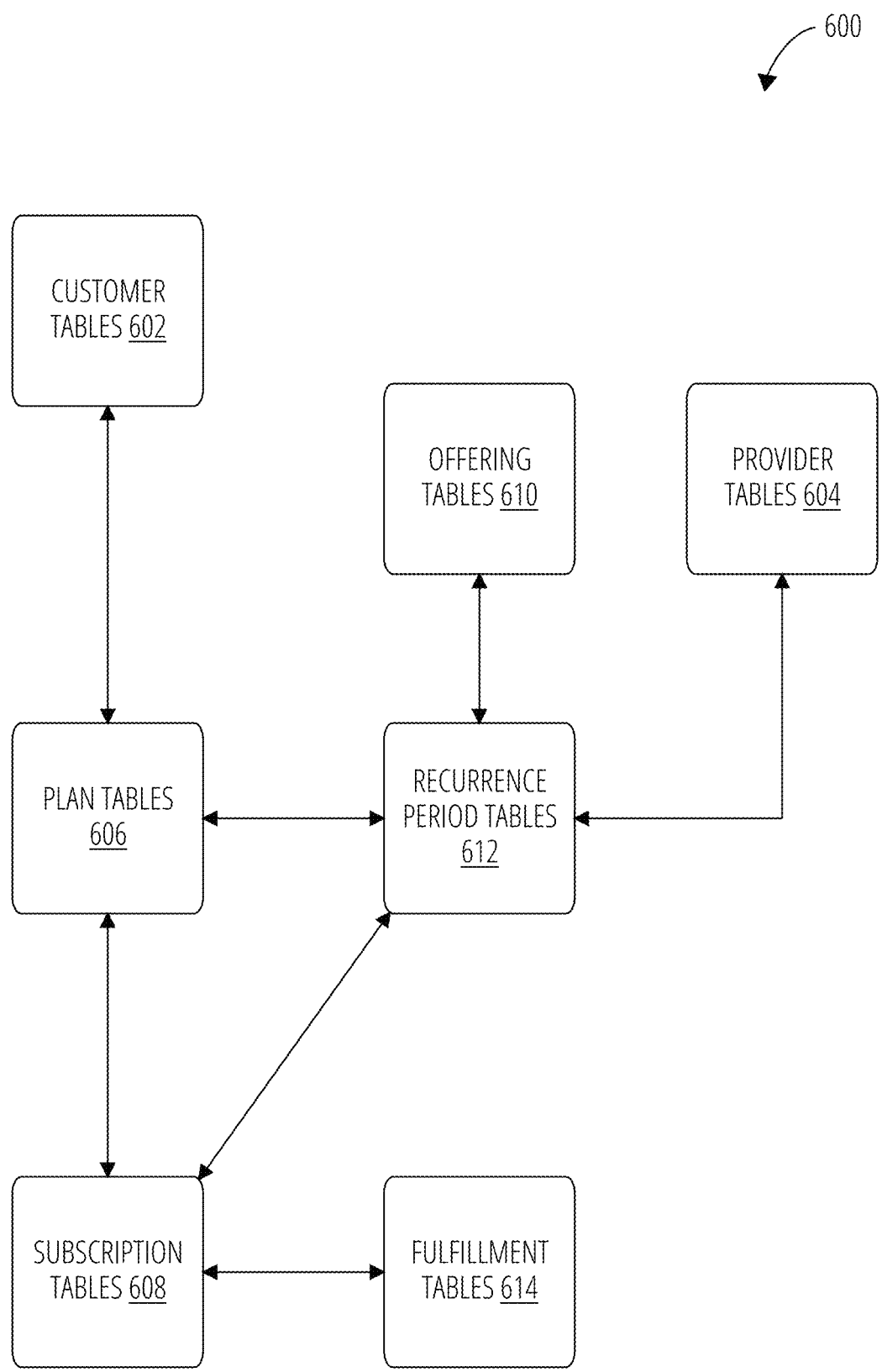
FIG. 6 is a block diagram as for details regarding a data architecture, according to some example embodiments.

FIG. 6 is a block diagram illustrating a data architecture 600, according to some example embodiments. The data architecture 600 is realized and stored within the database 148. Customer tables 602 store records for customers (e.g., the consumer or user 118) of various service providers, each service provider, in turn, being recorded within provider tables 604. A customer record within the customer tables 602 may be associated with a plan 502 for which a record exists within plan tables 606. Each plan 502 within the plan tables 606 may be associated with a set of subscriptions 504, records for which exist within the subscription tables 608. Offering tables 610 maintain records for each product/service 508 (as examples of offerings), and each subscription 506 has a specified cycle 514 within recurrence period tables 612. A fulfillment price 510 associated with a particular subscription 506 is also stored within respective records of the recurrence period tables 612.

Fulfillment records (e.g., indicating and recording whether a particular subscription 506 has been fulfilled) are stored within fulfillment tables 614.

Figure 7:
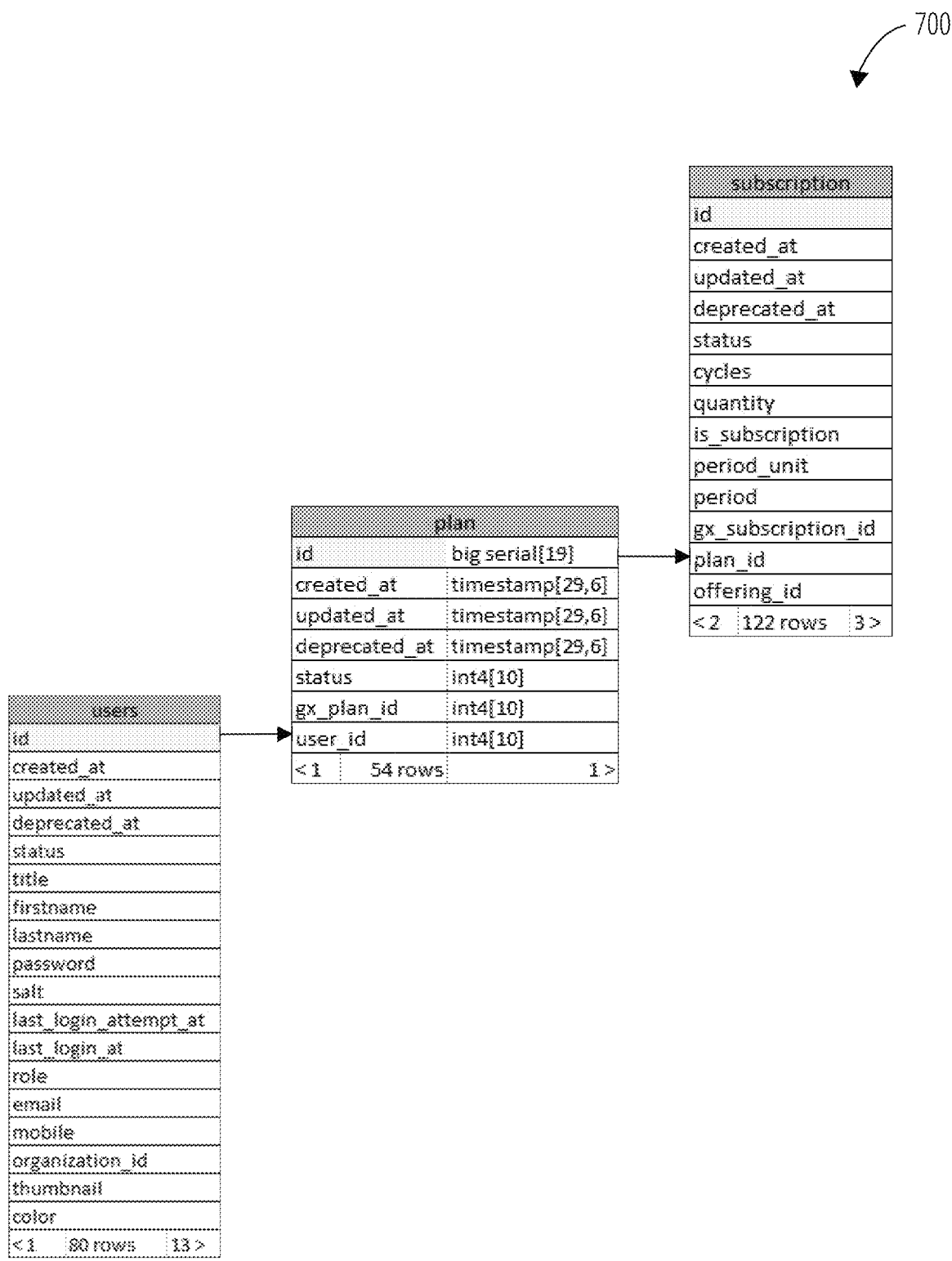
FIG. 7 is a table diagram illustrating further details of data, according to some example embodiments, stored within the various tables discussed above with reference to FIG. 6.

FIG. 7 is a table diagram 700 illustrating further details of data, according to some example embodiments, stored within the various tables discussed above with reference to FIG. 6.

Figure 8:
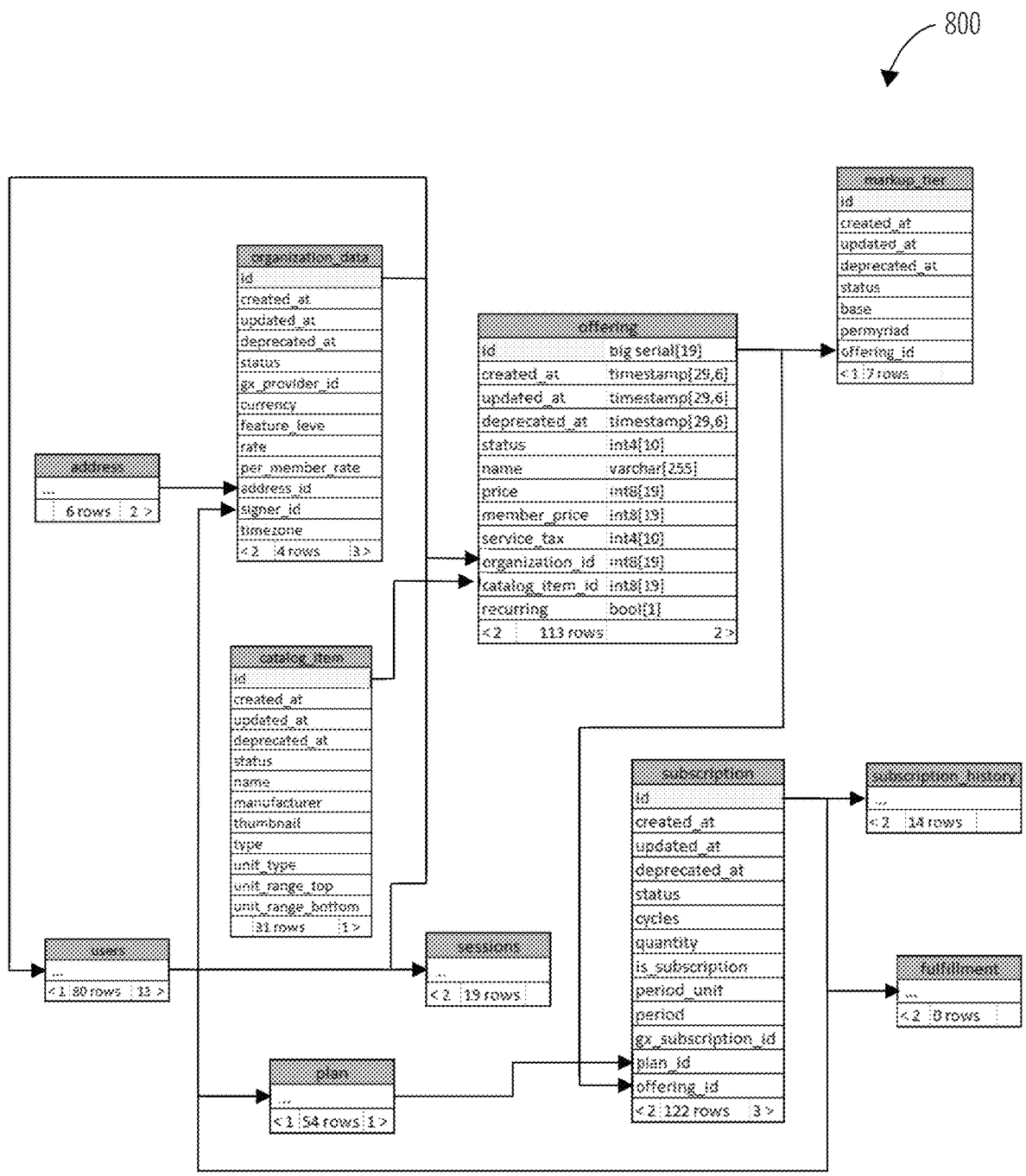
FIG. 8 is a table diagram illustrating further details of data, according to some example embodiments, stored within the various tables discussed above with reference to FIG. 6.

FIG. 8 is a table diagram 800 illustrating further details of data, according to some example embodiments, stored within the various tables discussed above with reference to FIG. 6.

Figure 9:
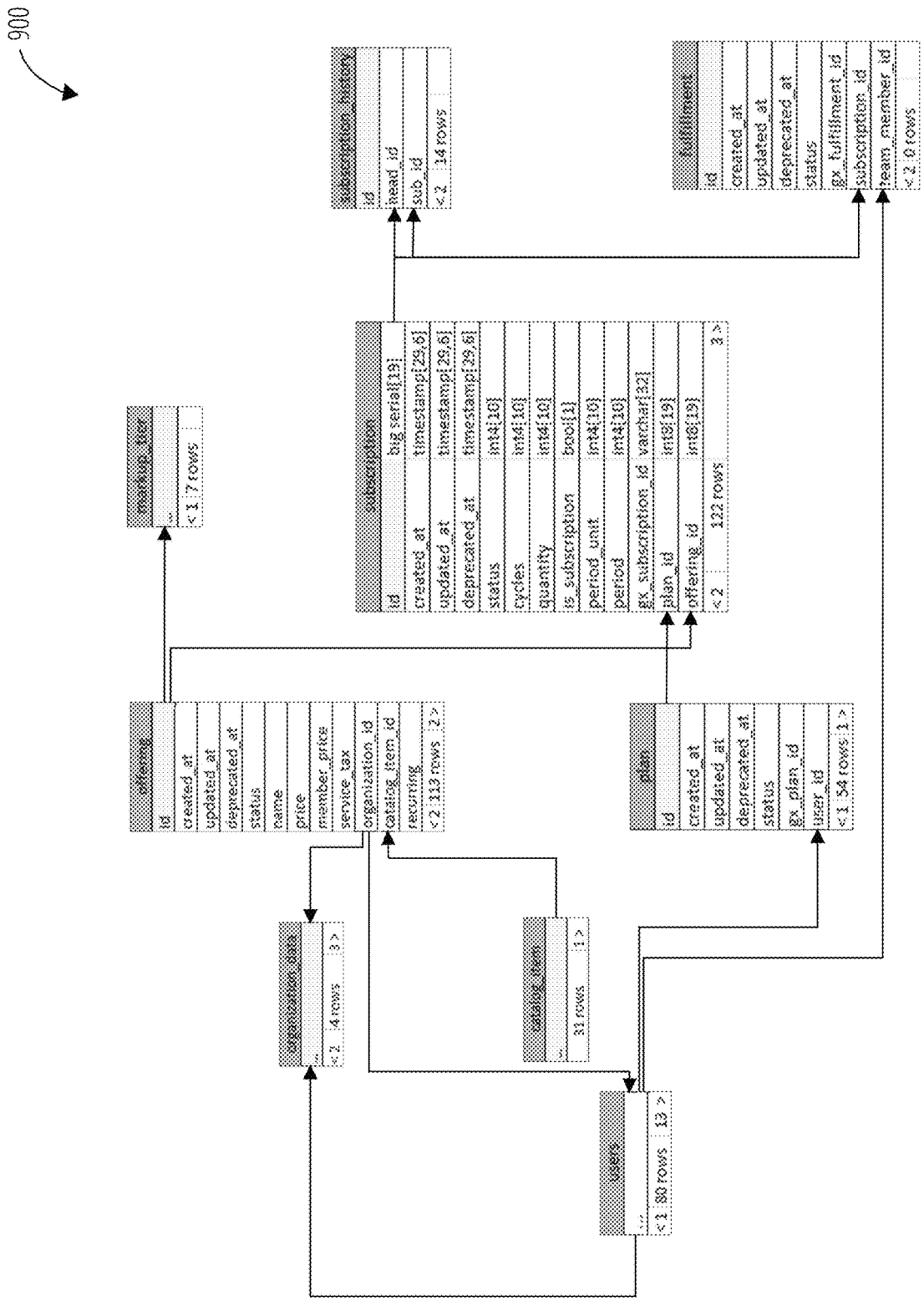
FIG. 9 is a table diagram illustrating further details of data, according to some example embodiments, stored within the various tables discussed above with reference to FIG. 6.

FIG. 9 is a table diagram 900 illustrating further details of data, according to some example embodiments, stored within the various tables discussed above with reference to FIG. 6.

Figure 10:
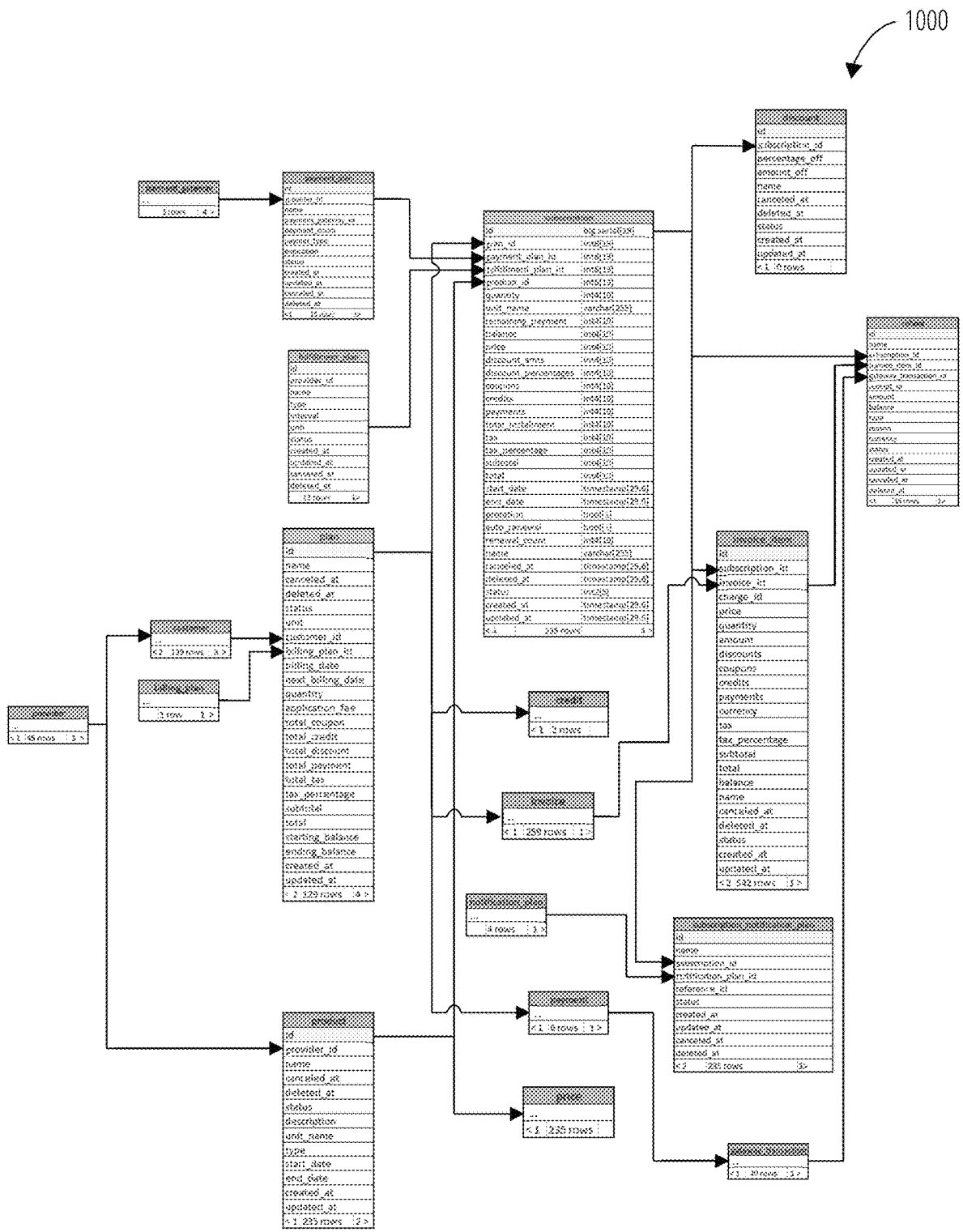
FIG. 10 is a table diagram illustrating further details of data, according to some example embodiments, stored within the various tables discussed above with reference to FIG. 6.

FIG. 10 is a table diagram 1000 illustrating further details of data, according to some example embodiments, stored within the various tables discussed above with reference to FIG. 6.

Figure 11:
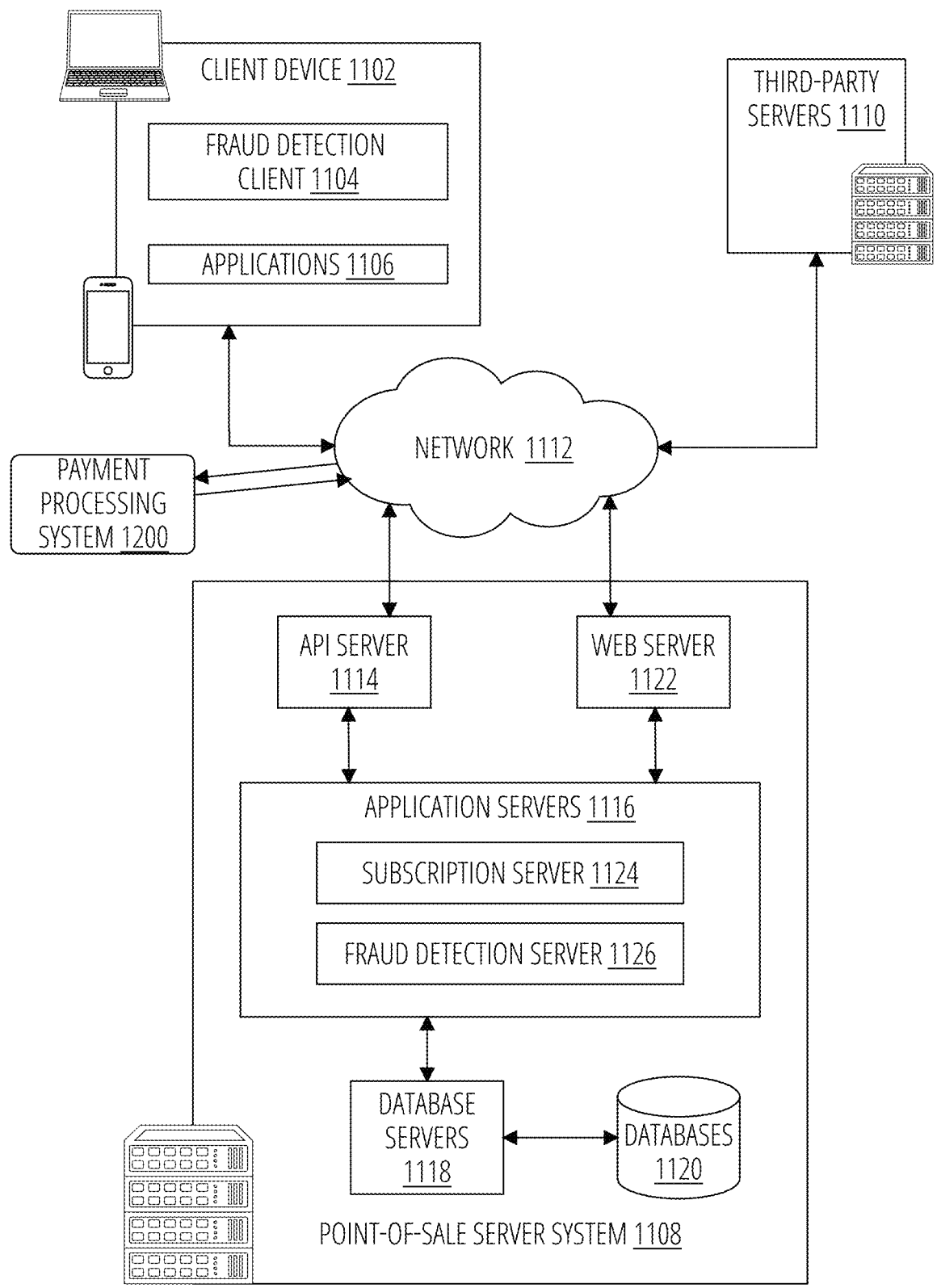
FIG. 11 is a block diagram showing an example point-of-sale system for conducting transactions over a network, according to some embodiments.

FIG. 11 is a block diagram showing an example point-of-sale system for conducting transactions over a network. The point-of-sale system is communicatively coupled to the payment processing system 1200 as part of the processing of card present payment transactions as described more fully below. The point-of-sale system includes multiple instances of a client device 1102, each of which hosts a number of applications, including a fraud detection client 1104 and other applications 1106. Each fraud detection client 1104 is communicatively coupled to other instances of the fraud detection client 1104 (e.g., hosted on respective other client devices 1102), a point-of-sale server system 1108, and third-party servers 1110 via a network 1112 (e.g., the Internet). The applications 1106 can also communicate with other locally-hosted applications 1106 using Applications Program Interfaces (APIs).

The point-of-sale server system 1108 provides server-side functionality via the network 1112 to a fraud detection client 1104. While certain functions of the point-of-sale system are described herein as being performed by either a fraud detection client 1104 or by the point-of-sale server system 1108, the location of certain functionality either within the fraud detection client 1104 or the point-of-sale server system 1108 may be a design choice. For example, it may be technically preferable to initially deploy certain technology and functionality within the point-of-sale server system 1108 but to later migrate this technology and functionality to the fraud detection client 1104 where a client device 1102 has sufficient processing capacity.

The point-of-sale server system 1108 supports various services and operations that are provided to the fraud detection client 1104. Such operations include transmitting data to, receiving data from, and processing data generated by the fraud detection client 1104. This data may include transaction data, customer data, product data, subscription data and provider data, as examples. Data exchanges within the point-of-sale server system 1108 are invoked and controlled through functions available via user interfaces (UIs) of the fraud detection client 1104.

Turning now specifically to the point-of-sale server system 1108, an API server 1114 is coupled to, and provides a programmatic interface to, application servers 1116. The application servers 1116 are communicatively coupled to a database server 1118, which facilitates access to a database 1120 that stores data associated with the transactions processed by the application servers 1116. Similarly, a web server 1122 is coupled to the application servers 1116 and provides web-based interfaces to the application server 1116. To this end, the web server 1122 processes incoming network requests over the Hypertext Transfer Protocol (HTTP) and several other related protocols.

The API server 1114 receives and transmits transaction data (e.g., commands and transaction data) between the client device 1102 and the application servers 1116. Specifically, the API server 1114 provides a set of interfaces (e.g., routines and protocols) that can be called or queried by the fraud detection client 1104 in order to invoke functionality of the application servers 1116. The API server 1114 exposes various functions supported by the application servers 1116, including account registration, subscription creations and management, the processing of transactions, via the application servers 1116, from a particular fraud detection client 1104 to another fraud detection client 1104.

The application servers 1116 host a number of server applications and subsystems, including, for example, a subscription server 1124 and a fraud detection server 1126. The subscription server 1124 implements functionalities for creating and managing subscriptions between multiple client devices 1102.

The fraud detection server 1126 provides functionalities for pre-declining fraudulent card transactions based on an evaluation of the transaction. Further details regarding the fraud detection server 1126 are provided below.

Figure 12:
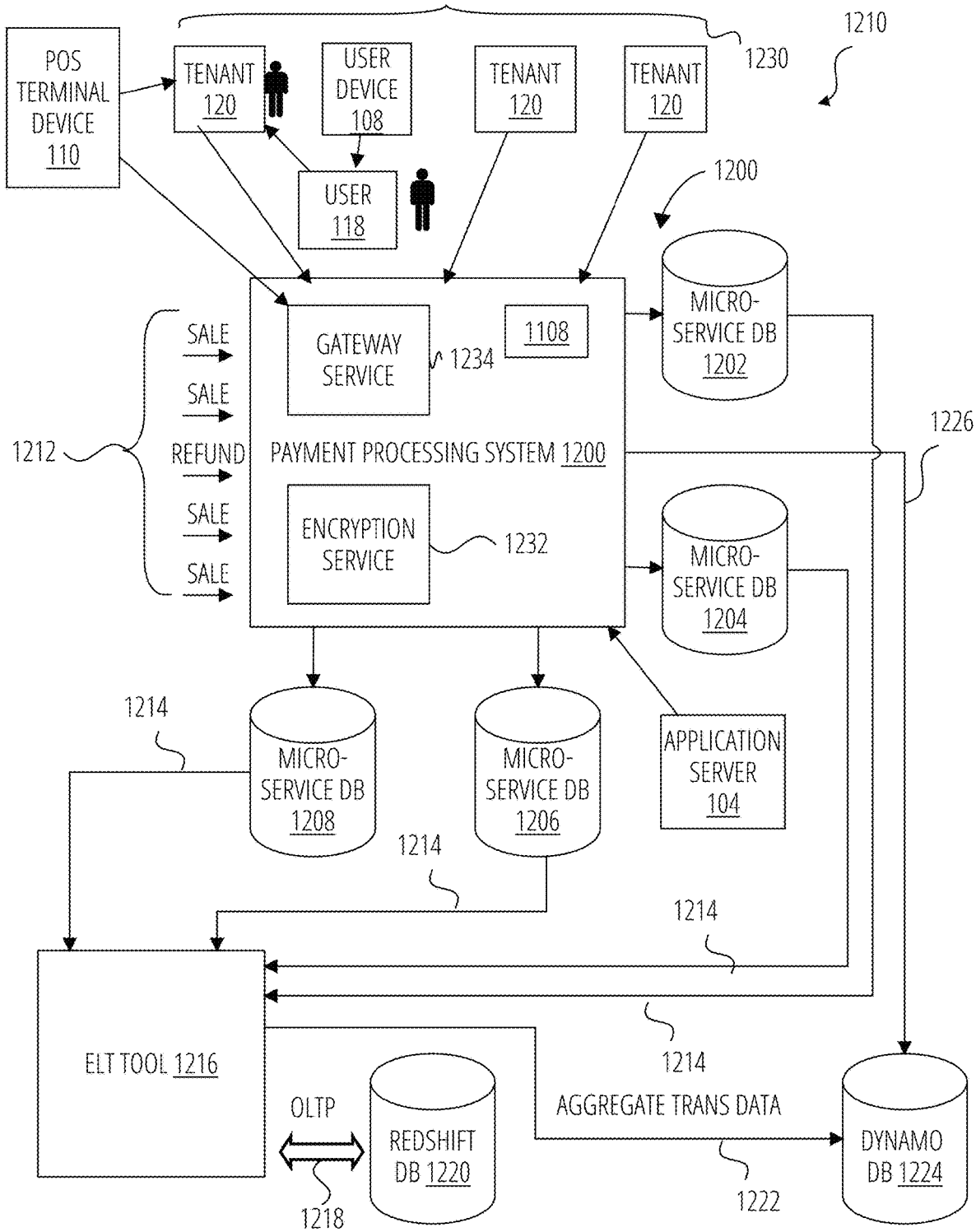
FIG. 12 is a block diagram illustrating a networked environment in which the described technology, according to some example embodiments, may be deployed.

With reference to FIG. 12, in some examples, the point-of-sale server system 1108 is included in a payment processing system 1200 or conglomerate of payment systems. The payment processing system 1200 may include payment deduplicating and fraud-detecting functionality. The payment processing system 1200 processes payment or transaction data.

In relation to fraud detection operations, the payment processing system 1200 may operate as or include a microservices depot including connections to one or more microservices databases, for example, including the illustrated microservice databases 1202, 1204, 1206, and 1208. The payment processing system 1200 and microservice databases may operate in a multi-tenant network 1210 including at least one tenant 120, as an example tenant (e.g., tenant 120 of FIG. 1) in the multi-tenant network 1210. The tenant 120 may serve a consumer or patient (for example the user 118 of FIG. 1) and seek to receive a payment from this party for a subscription, item, or service, for example.

In some examples, the payment processing system 1200 includes a number of microsystems that each provide an associated microservice for a given tenant in the multitenant environment. Example microservices may include a point-to-point (P2P) encryption microservice (that writes to the microservice database 1202, for example), a global gateway microservice (that writes to the microservice database 1204, for example), a card microservice (that writes to the microservice database 1206, for example), and a payment microservice (that writes to the microservice database 1208, for example). Other microservices are possible.

In an example transaction, a patient at the tenant 120 swipes a card to pay for a product or service. Many other different types of transactions 1212 (such as sales (purchase), refunds, credits, loyalty program redemptions and so forth) may be received from any one or more of the patients at any one of more of the tenants in the multi-tenant network 1210. The numbers of patients and tenants can run into the thousands or even millions. It will be appreciated that the number, variety, and complexity of the transactions 1212 can be very high. In some examples, the payment processing system 1200 is configured to process this great multiplicity of transactions to check for fraud in near real-time.

When the example transaction is received at the tenant 120, at least one of the microservices in the payment processing system 1200 is invoked based on the nature or type of the transaction and writes out to its associated microservice database. As the transactions 1212 each proceed, each microservice database 1202-1208 collects its own related part of the transaction information; for example, the microservice database 1208 collects information for payment transactions (e.g., cash transactions), while the microservice database 1206 collects information for credit or debit card transactions. Other microservices are possible.

In some examples, the microservices depot includes a further microservice (not shown) called a ledger microservice. An associated ledger microservice database stores aspects related to transactional bookkeeping, recording aspects such as a transaction ID, a transaction dollar amount, details of an item, product or service purchased, and so forth. The ledger microservice operates as a ledger and keeps a tally of such details. The ledger information may be distributed or shared with all the other microservices.

In some examples, the data stored in microservice database 1202-1208 is transmitted (or otherwise made available) at operation 1214 to an "extract, load and transform" (ELT) tool, such as the illustrated ELT tool 1216. An example ELT tool 1216 may be (or include) a Matillion™ ELT tool 1216. For all of the microservices (including the ledger microservice), the ELT tool 1216 can perform ELT operations based on the continuous data supplied to it from the microservices databases 1202, 1204, 1206, and 1208, including, in some examples, the ledger microservice database.

In some examples, an output 1218 of the ELT tool 1216 includes normalized data or online transaction processing (OLTP) data that has been extracted, loaded, and transformed into star schemas and stored in a database, such as the Redshift database 1220. In some examples, the ELT tool 1216 extracts OLTP data, data from external online transaction processing databases, and data from any one or all of the microservice databases; loads the data; transforms this data into an abstracted, online analytical processing structure; and stores this as one or more star schemas in the Redshift database 1220.

In some examples, in parallel with the ELT process, the ELT tool 1216 also aggregates transactional information as part of its transformation, and then pushes at operation 1222 this aggregated data for storage in a Dynamo database 1224. In one sense, this operation may be considered to be moving information from what is a reporting infrastructure into a transaction processing resource. At operation 1226, the payment processing system 1200 and each of the microservices have access to this Dynamo database 1224 for fraud detection purposes and evaluation against near real-time aggregated information and ongoing real-time transactions 1212.

This aggregation of transactional data allows for the creation of fraud detection rules or threshold fraud parameters. Rules or threshold parameters may be based, for example, on an average monthly volume per practice for an individual practice (tenant) or patient. Other rules and thresholds are described further below in connection with machine learning with reference to FIG. 13.

As opposed merely to providing fixed fraud detection rules or threshold parameters, some examples allow for dynamic rule setting and flexibility in configuration. Assume a new practice joins a medical network as an example multitenant environment. Here, based on the type of practice it is and based on what has been seen historically across sets of practices, examples allow different machine learning algorithms to predict what an average sales price for use as a fraud detection trigger might be for the new practice. The new practice can be immediately protected and "inherit" existing rules and threshold parameters, accordingly.

Examples can also predict that a purchase, for example a neurotoxin like Botox, includes a certain average reorder time or purchase frequency. A purported reorder transaction for the same product that is received in too short a time, or at an increased frequency, is potentially fraudulent. Based on such purchase patterns, fraud scores for a given transaction can be developed and processed, accordingly. This is described in greater detail below with reference to FIG. 13.

In relation to payment deduplication functionality, some examples of a payment processing system 1200 herein generate an alert based on a detection that multiple payments are being issued for the same purchase of a subscription, item or service in order to prevent multiple payments being collected for the same purchase. Examples seek to provide a technical solution assisting users to prevent re-running multiple payments for the same purchase, either inadvertently or due to system glitches.

In this regard, the payment processing system 1200 includes at least one processor and a memory storing instructions that, when executed by the at least processor, cause the payment processing system 1200 to perform operations comprising detecting a card-present (CP) transaction request that comprises a set of CP transaction data, the CP transaction request relating to a purchase of an item or service and initiated by a card swipe or card tap made by human user (for example, user 118) at a Point-of-Sale POS terminal device 110 device operating at a tenant (for example a tenant 120) in a multi-tenant network (for example multi-tenant network 1210); accessing the CP transaction data; monitoring a flow of the CP transaction data across a plurality of communicatively-coupled CP transaction processing components, the CP transaction processing components including at least the POS terminal device 110, a federation layer 1230 executing between tenants 120 in the multi-tenant network 1210, a peer-to-peer encryption service 1232 accessible by the POS terminal device 110 and invoked by the CP transaction request, a gateway service 1234 acting as an exclusive contact point for the POS terminal device 110, and an application-support server (for example, application server 104) executing or processing data for a payment application to present at least some of the CP transaction data in a user interface of a mobile device (for example, user device 108) operated by the human user; detecting a failure or breakdown in the flow of monitored CP transaction data; detecting an attempted re-initiation of the CP transaction request for the same purchase of the item or service, the attempted re-initiation of the CP transaction request made after the detected failure or breakdown in the flow of monitored CP transaction data, the re-initiated CP transaction request including re-initiated CP transaction data; accessing the re-initiated CP transaction data; based on the detected re-initiation of the CP transaction request, comparing the CP transaction data against the re-initiated CP transaction data to identify an attempted duplicated payment for the purchase of the item or service; and based on the identified attempted duplicated payment, initiating a payment deduplication phase by generating a potential payment duplication alert for presentation at the POS terminal device 110 and/or in the user interface of the user device 108 operated by the human user.

In some examples, the operations further comprise, based on a response to the payment duplication alert, progressing the payment deduplication phase by voiding, or facilitating a voiding of, either one of the initial and re-initiated CP transaction requests. In some examples, progressing the payment deduplication phase further comprises processing a non-voided initial or re-initiated CP transaction request. In some examples, the response to the potential payment deduplication alert is received at the POS terminal device 110. In some examples, the response to the potential payment deduplication alert is received from the mobile device (user device 108) operated by the human user.

In some examples, comparing the CP transaction data against the re-initiated CP transaction data further comprises inputting the CP transaction data into a machine-learned model trained to analyze a set of historical transaction data, the set of historical transaction data having been aggregated from one or more historical data sources, the one or more historical data sources including at least one microservice database collecting a particular aspect of transactional data processed by a corresponding microservice of the tenant in the multi-tenant network; using an output of the machine-learned model to generate a transaction comparison fingerprint based on common or repeated tenant or human user payment transactions; storing the transaction comparison fingerprint in a transaction comparison fingerprint cache table, and monitoring a frequency or number of times the CP transaction data matches a transaction comparison fingerprint; comparing the CP transaction data against at least one transaction comparison fingerprint in the transaction comparison fingerprint cache table to generate a comparison result; and based on the comparison result, or the monitored frequency or number of matches, generating the potential payment duplication alert.

In some examples, monitoring the flow of the CP transaction data across the plurality of communicatively-coupled CP transaction process components includes monitoring for a failure or breakdown including at least one of a card decline, a network error, a request time out, a gateway time out, a failed response receipt, a bank error, a processor error, a lost connection, a power loss, a device reboot, and a device restart. In some examples, the tenant in the multi-tenant network is an aesthetic medical practice in a network of medical service providers, and wherein the human user is a patient at the aesthetic medical practice.

Figure 13:
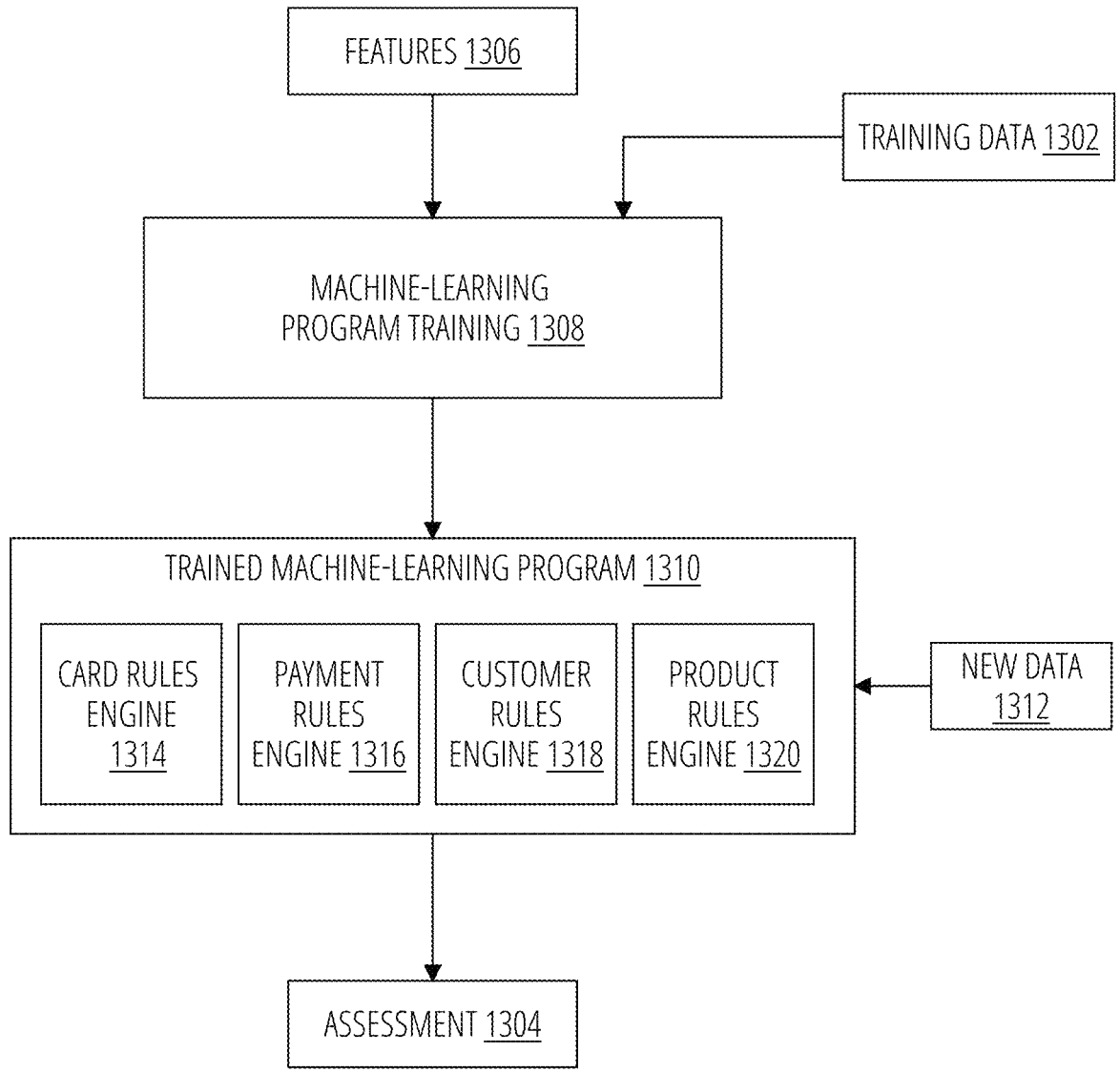
FIG. 13 illustrates the training and use of a machine-learning program, according to some embodiments.

FIG. 13 illustrates the training and use of a machine-learning program, according to some embodiments that may be used in conjunction with the fraud detection and payment deduplication (e.g., fingerprint generation) operations discussed above in connection with FIG. 12. In some embodiments, machine-learning programs (MLPs), also referred to as machine-learning algorithms or tools, are utilized to perform operations associated with malware classification. Machine learning is a field of study that gives computers the ability to learn without being explicitly programmed. Machine learning explores the study and construction of algorithms, also referred to herein as tools, that may learn from existing data and make predictions about new data. Such machine-learning tools operate by building a model from example training data 1302 in order to make data-driven predictions or decisions expressed as outputs or assessment 1304. Although some embodiments are presented with respect to a few machine-learning tools, the principles presented herein may be applied to other machine-learning tools.

In some embodiments, different machine learning tools may be used. For example, Logistic Regression (LR), Naive-Bayes, Random Forest (RF), neural networks (NN), matrix factorization, and Support Vector Machines (SVM) tools may be used for classifying or scoring transaction data.

Two common types of problems in machine learning are classification problems and regression problems. Classification problems, also referred to as categorization problems, aim at classifying items into one of several category values (for example, is this object an apple or an orange?). Regression algorithms aim at quantifying some items (for example, by providing a value that is a real number). In some embodiments, example machine-learning algorithms provide a prediction probability to classify an image as digitally manipulated or not. The machine-learning algorithms utilize the training data 1302 to find correlations among identified features 1306 that affect the outcome.

The machine-learning algorithms utilize features 1306 for analyzing the data to generate an assessment 1304. The features 1306 are an individual measurable property of a phenomenon being observed. The concept of a feature is related to that of an explanatory variable used in statistical techniques such as linear regression. Choosing informative, discriminating, and independent features is important for effective operation of the MLP in pattern recognition, classification, and regression. Features may be of different types, such as numeric features, strings, and graphs. In one embodiment, the features 1306 may be of different types. For example, the features 1306 may be features of historical transaction data.

The machine-learning algorithms utilize the training data 1302 to find correlations among the identified features 1306 that affect the outcome or assessment 1304. In some embodiments, the training data 1302 includes labeled data, which is known data for one or more identified features 1306 and one or more outcomes, such as detecting fraudulent transactions.

With the training data 1302 and the identified features 1306, the machine learning tool is trained during machine-learning program training 1308. Specifically, during machine-learning program training 1308, the machine-learning tool appraises the value of the features 1306 as they correlate to the training data 1302. The result of the training is the trained machine-learning program 1310.

When the trained machine-learning program 1310 is used to perform an assessment, new data 1312 is provided as an input to the trained machine-learning program 1310, and the trained machine-learning program 1310 generates the assessment 1304 as output. For example, when transaction data is received, the historical transaction data is accessed, and the weights of the corresponding data sources are computed, the machine-learning program utilizes features of the historical transaction data to determine if the received transaction request is fraudulent or not.

In some examples, the trained machine-learning program 1310 includes a series of rules engines. Each rules engine includes a list of rules that the incoming transaction request is evaluated against before providing the assessment 1304. For example, the trained machine-learning program 1310 may include a card rules engine 1314, a payment rules engine 1316, a customer rules engine 1318, and a product rules engine 1320. The card rules engine 1314 includes a set of rules that the card data associated with transaction request must be evaluated against before providing the assessment 1304. The payment rules engine 1316 includes a set of rules that the payment data associated with the transaction request must be evaluated against before providing the assessment 1304. The customer rules engine 1318 includes a set of rules that the customer data associated with the transaction must be evaluated against before providing the assessment 1304. The product rules engine 1320 includes a set of rules that the product data must be evaluated against before providing the assessment 1304.

In some examples, payment transaction data or a fingerprint may be based on or include one or more of a merchant (tenant) ID, a patient (user) ID, or an amount of time, for example a payment transaction including these three value fields performed within a value X of a monitored time period or frequency, where X is a configurable value.

In some examples, training data for machine learning purposes is aggregated and encrypted (or anonymized) in a multitenant environment. Some fraud detection examples relate to or include data aggregation and anonymization in multi-tenant networks or networks and, in some examples, to a data aggregator and anonymizer that can encrypt sensitive data received from multiple tenants as data sources. The sensitive data may include Personally Identifiable Information (PII), Protected Health Information (PHI) and Payment Card Industry (PCI) information. In some examples, anonymized data can be aggregated for multi-faceted testing without disclosing sensitive aspects. In some examples, the aggregated data can be selectively unencrypted to a given tenant.

Results derived from an analysis of "big data" can generally be improved if the volume of test data is significant. Typically, the larger the volume of test data, the more accurate an analysis of it will be. For example, there is greater chance to identify data outliers and trends in a significant body of data. Data aggregation, however, is not easy. It may be aggregated from different sources, but each source will likely have different methods of data protection with which to comply. Each source will also very often have different data content and configuration, and this may conflict with data configuration of other sources. This aggregation of disparate sources of protected information presents technical challenges, particularly in multi-tenant networks or environments. The more data that is collected, the more complicated the security protocols become and the greater the risk of inadvertent disclosure or malicious access to it. Great care is required not to disclose encrypted information to third-party sources of aggregated data, or third-party "big data" analyzers scrutinizing collected data for discernible trends or machine-learning purposes, for example.

According to some example embodiments, techniques and systems are provided for data aggregation and anonymization in multi-tenant networks or environments. In some examples, a data aggregator and anonymizer platform can encrypt sensitive data received from multiple tenants as data sources. The sensitive data may include PII, PHI, and PCI information. In some examples, anonymized data can be aggregated for multi-faceted testing without disclosing sensitive aspects. In some examples, a portion of the aggregated data can be selectively unencrypted and returned or presented to a tenant that was the original source or keeper of that portion of the aggregated data. The remainder of the portions are not unencrypted and may continue to form part of a body of test data.

Fundamental problems that may arise when processing data in strict compliance to a regulated environment, involving PPI, PHI, or PCI for example, can occur at a confluence of healthcare and treatment information records. One challenge includes simulating a set of problems in production data using test data. For a single medical practice, for example, subscribing along with other medical practices (tenants) to a subscription service (for example) in a multi-tenant network, using a small set of test data based on its own production data may limit the body of test data that can be assembled. On the other hand, trying to build a bigger set of test data by incorporating data from other tenants accessible in the multi-tenant network runs a serious risk of privacy invasion and breach of compliance laws. Further, a desire to collect a large body of data for testing and analysis may include sourcing data that is external to the multi-tenant network and may involve the participation of third parties to analyze the data (e.g., "big data" analysis). Thus, data protection laws prevent a mere aggregation of production data for test purposes.

In other aspects, a further challenge is to simulate realistically, in test environments, what is really happening in production environments. It is difficult to obtain a representative sample of test data that actually and realistically reflects production conditions of whatever aspect the tenant may be developing (for example, an updated health service to patients, a new product offering, or an enhanced online functionality).

In further challenging aspects, production and test systems usually have layers. Lower layers can be accessed by many people, while higher layers can be accessed by relatively few. Access and security protocols differ across layers. In a regulated environment, one cannot easily bring down test information into lower layers because this may violate one or more compliance laws since wider access to this information is provided.

In order to address these and other challenges, some present examples, at a high level, classify and encrypt test information, in particular sensitive information contained in the test information, before it is brought down to lower layers. A representative sample of anonymized test data is made available for testing and, in some examples, is configurable based on data fields that might remain or are encrypted, among other factors. Once the encrypted information is brought down to lower layers, the anonymized test data may be used for a variety of testing purposes during development of a service or product, as discussed above.

Some present examples aggregate data to create a body of test data. The aggregated data may include data sourced from sources other than a single tenant (in other words, an aggregation of multi-tenant or multi-party data). For testing purposes, data analysis, or machine training purposes, an enhanced body of test data may be useful to a tenant or third-party data analyzer even though not all of the aggregated data may have been sourced from it. In this situation, a complicated cross-matrix of protection protocols such a PII, PHI, and PCI may apply, and each tenant may be entitled only to view the portion of the data that it supplied (or at least view an unencrypted version of that data). Present examples of a data aggregator and anonymizer platform facilitate the creation and access to such combined test data, yet still allow and greatly facilitate compliance with data protection laws in doing so.

In cloud-based and other modern systems (e.g., Software-as-a-Service (SaaS) platforms and so forth), most enterprises rely very heavily on third-party applications to process data. Some of these applications may include "big data" processing systems. The enterprise cannot physically control what these third parties do with their data. While inter-party agreements restricting data access and publication may be established, there is always a possibility of a rogue actor acting outside the agreed terms. A rogue actor at one tenant in a multi-tenant network might use network credentials to access another tenant to look up prohibited data. The accessed data might be used for exploitation or ransomware purposes, for example.

Thus, in some present examples, a data aggregator and anonymizer can aggregate and provide anonymized data that, even if accessed by a rogue actor, does not contain any identifying information. In some examples, a data encryption key is used to encrypt test data. In some examples, a decryption key to unlock test data is destroyed. In some examples, a decryption key to unlock a portion of aggregated test data is provided only to the tenant supplying that portion. The decryption key disallows decryption of any other data. The tenant as a source of data is thus placed in the same (unencrypted) position it was before supplying a portion of data to be aggregated, yet has enjoyed the benefit of results and analysis derived from a much larger body of test data sourced from many other, if not all, tenants in a multi-tenant network. The tenants are reassured that any contributed data that has been aggregated and shared with another tenant or third-party data analyzer has nevertheless remained encrypted for purposes such as testing, "big data" analysis, machine learning, and so forth.

Figure 14:
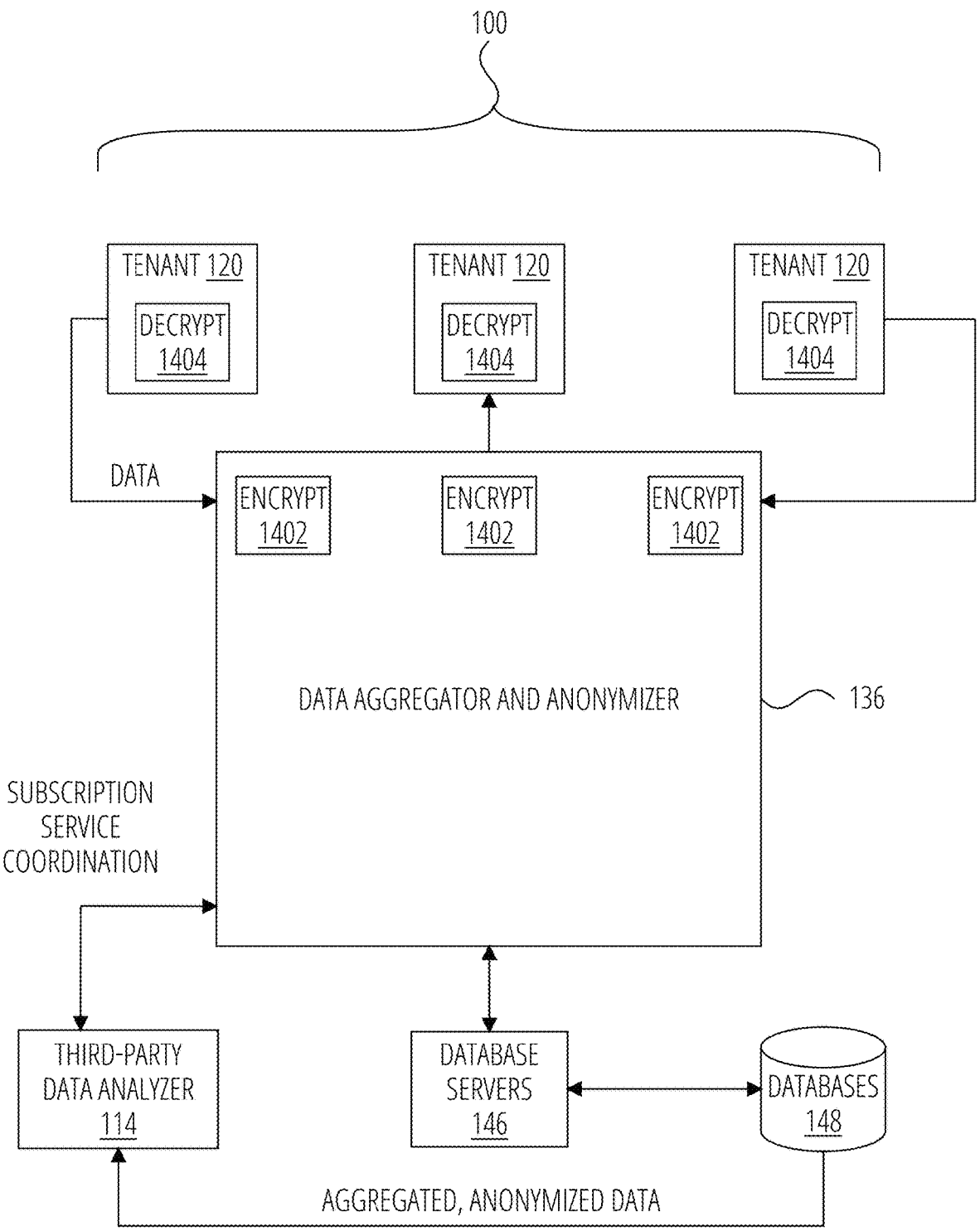
FIG. 14 illustrates a networked environment in which the described technology, according to some example embodiments, may be deployed.

With reference to FIG. 14, in some examples, a tenant 120 in a multi-tenant network 100 may wish to create a testing environment in which to develop a new product or service. To that end, in present examples, the tenant 120 can contact the subscription service 106 and request an aggregation of test data or an analysis of a body of data to help in developing the product or service. The subscription service 106 invokes the data aggregator and anonymizer 136 shown in the view. The tenant 120 may contribute some data, such as production data, to be aggregated or anonymized for test purposes. Some of this production data may be covered by PII, PHI, or PCI requirements and will therefore require appropriate treatment before it can be analyzed by or shared with others. As described more fully below, the aggregated test data is classified to identify sensitive data and encrypted accordingly. The test data is aggregated by the data aggregator and anonymizer 136 to assist in simulating production conditions in which to test the tenant's proposed product or service. In some examples, a plurality of tenants 120 may request an analysis of their respective production data or a simulation of a real-life real-time production environment.

The data aggregated by the data aggregator and anonymizer 136 may be derived from a number of different data sources to assist in creating a realistic test environment or a rich body of data for analysis and training, for example. In some examples, the data may be sourced from a number of sources, without limitation. A data source may include, for example, a single tenant in a network, a plurality of tenants in a network, a single third party outside of a network, or a plurality of third parties outside of a network. Tenants or third parties may be sources of application data, web-based traffic data, or other types of data. Tenants and third parties may offer analysis tools and machine learning models, or other services.

Whether requested by a single tenant 120, or several tenants 120, the aggregated data may comprise a complicated cross-matrix of protection protocols such as PII, PHI, and PCI. Each tenant 120 may be entitled only to view a portion of the data that it supplied or, if permitted, an unencrypted version of that data.

In some examples, data sent by a tenant or accessed by the data aggregator and anonymizer 136 is encrypted at 1402 upon receipt or a grant of access. In some examples, when test data, or analyzed data results, are sent back to a tenant 120, this portion of the data is decrypted at 1404. These processes are described more fully below. The aggregated and anonymized data is stored in a database, such as the one or more databases 148 described above. Present examples of a data aggregator and anonymizer 136 facilitate the creation and access to combined test data, yet still allow and greatly facilitate compliance with data protection laws in so doing.

In some examples, one or more third-party data analyzers 114 may request access to the aggregated and anonymized data stored in the database 148 for purposes of analyzing it to support the tenant's product or service development mentioned above. A third-party data analyzer 114 may be contracted by the subscription service 106, or a tenant 120, to perform data analysis. With appropriate authorization, the third-party data analyzer 114 may be granted access to the data stored in the database 148. To the extent any access is granted, or to the extent a rogue actor may be at work, the aggregated data stored in the database 148 remains anonymized and yields no sensitive information. The data stored in the database 148 may be safely used by the third-party data analyzer 114, or a tenant 120, or the data aggregator and anonymizer 136, in a number of ways including, for example, data analysis, the development of models for machine learning, and for other purposes.

Figure 15:
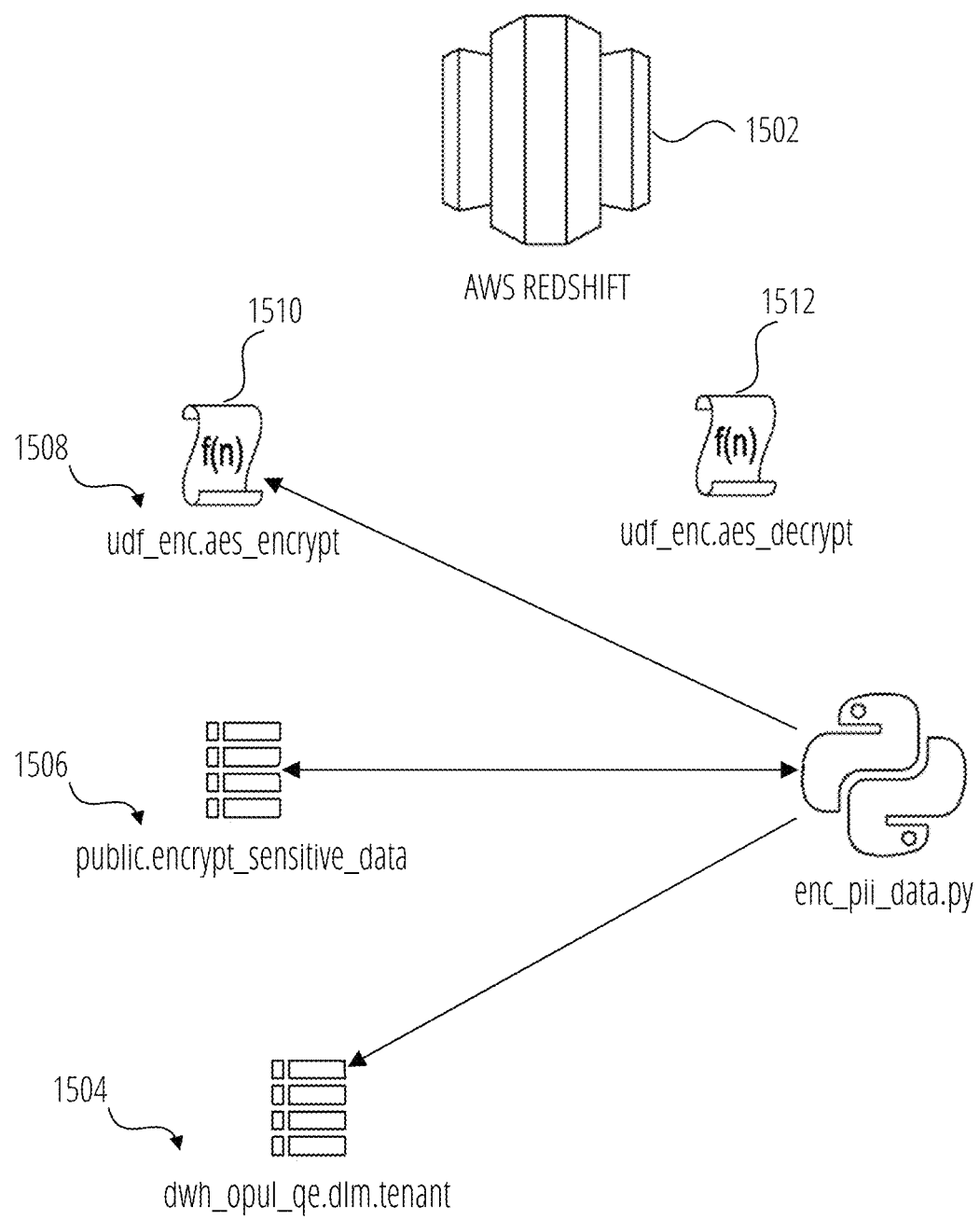
FIG. 15 is a schematic diagram illustrating aspects of encryption, according to some examples.

With reference to FIG. 15, some examples, particularly those that utilize the cloud or cloud-based services, include layers, such as software, application, or storage layers, responsible for or utilized in certain aspects of data usage and processing from an origin to post-production. One aspect includes encryption. An example encryption can include an Advanced Encryption Standard (AES). AES follows a symmetric encryption algorithm, i.e., the same key is used to encrypt and decrypt the data. AES supports block lengths of 528, 592, and 556 bits. One example, in a data analytics or reporting tier, includes Amazon Web Services (AWS) Redshift 1502 for encryption and decryption. Redshift is used in some examples to encrypt and decrypt data in various layers. Other encryption software is possible.

In some examples, an AES encryption level is specific to a database persistence layer, for example as shown in FIG. 15. At a first layer 1504, stored data is sourced from one or more tenants 120 and aggregated. At layer 1506, sensitive data in the aggregated data is identified and encrypted. These operations may occur at the data aggregator and anonymizer 136 using database 148 (FIG. 1), for example. Sensitive data is scrambled, hashed, or randomly keyed in some examples. At layer 1508 (for example a lower, widely distributed layer), data is encrypted at 1510 so that it is rendered anonymous. Users operating in this lower level layer 1508 have no access to sensitive data, or if access is obtained, the data is meaningless because it has been anonymized. The data can be decrypted at 1512 as needed for authorized provision to a tenant seeking full access to their data. These encrypt/decrypt operations may occur at the data aggregator and anonymizer 136 or at a tenant 120 (FIG. 1), in some examples. The aggregated, anonymized data may be stored in database 148 (FIG. 1).

Figure 16:
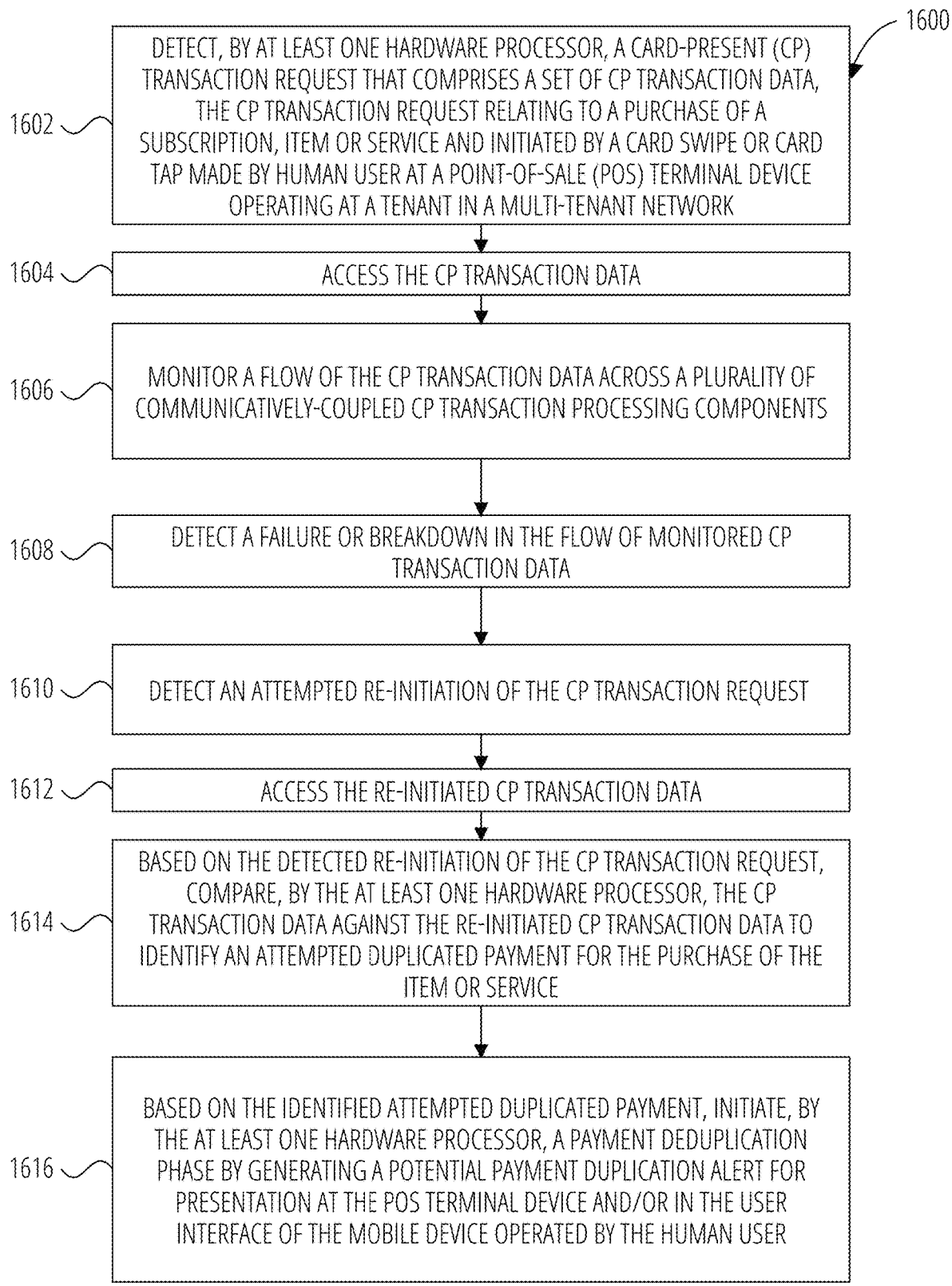
FIG. 16 illustrates a method 1600 in accordance with one embodiment.

FIG. 16 is a flowchart illustrating a payment deduplication method 1600, according to some example embodiments, that seeks to avoid multiple payments for the same purchase of a subscription, item or service, for example. Although the described flow diagram below can show operations as a sequential process, many of the operations can be performed in parallel or concurrently. In addition, the order of the operations may be re-arranged. A process is terminated when its operations are completed. A process may correspond to a method, a procedure, an algorithm, etc. The operations of methods may be performed in whole or in part, may be performed in conjunction with some or all of the operations in other methods, and may be performed by any number of different systems, such as the systems described herein, or any portion thereof, such as a processor included in any of the systems.

In operation 1602, method 1600 detects, by at least one hardware processor, a card-present (CP) transaction request that comprises a set of CP transaction data, the CP transaction request relating to a purchase of a subscription, item or service and initiated by a card swipe or card tap made by human user at a point-of-sale (POS) terminal device operating at a tenant in a multi-tenant network. In operation 1604, method 1600 accesses the CP transaction data. In operation 1606, method 1600 monitors a flow of the CP transaction data across a plurality of communicatively-coupled CP transaction processing components, the CP transaction processing components including at least the POS terminal device, a federation layer executing between tenants in the multi-tenant network, a peer-to-peer encryption service accessible by the POS terminal device and invoked by the CP transaction request, a gateway service acting as an exclusive contact point for the POS terminal device, and an application-support device executing or processing data for a payment application to present at least some of the CP transaction data in a user interface of a mobile device operated by the human user. In operation 1608, method 1600 detects a failure or breakdown in the flow of monitored CP transaction data. In operation 1610, method 1600 detects an attempted re-initiation of the CP transaction request for the same purchase of the item or service, the attempted re-initiation of the CP transaction request made after the detected failure or breakdown in the flow of monitored CP transaction data, the re-initiated CP transaction request including re-initiated CP transaction data. In operation 1612, method 1600 accesses the re-initiated CP transaction data. In operation 1614, method 1600 based on the detected re-initiation of the CP transaction request, compares, by the at least one hardware processor, the CP transaction data against the re-initiated CP transaction data to identify an attempted duplicated payment for the purchase of the item or service. In operation 1616, method 1600 based on the identified attempted duplicated payment, initiates, by the at least one hardware processor, a payment deduplication phase by generating a potential payment duplication alert for presentation at the POS terminal device and/or in the user interface of the mobile device operated by the human user.

In some examples, the method 1600 further comprises, based on a response to the payment duplication alert, progressing the payment deduplication phase by voiding, or facilitating a voiding of, either one of the initial and re-initiated CP transaction requests. In some examples, progressing the payment deduplication phase further comprises processing a respective non-voided initial or re-initiated CP transaction request.

In some examples, the response to the potential payment deduplication alert is received at the POS terminal device. In some examples, the response to the potential payment deduplication alert is received from the mobile device operated by the human user.

In some examples, comparing the CP transaction data against the re-initiated CP transaction data further comprises: inputting the CP transaction data into a machine-learned model trained to analyze a set of historical transaction data, the set of historical transaction data having been aggregated from one or more historical data sources, the one or more historical data sources including at least one microservice database collecting a particular aspect of transactional data processed by a corresponding microservice of the tenant in the multi-tenant network; using an output of the machine-learned model to generate a transaction comparison fingerprint based on common or repeated tenant or human user payment transactions; storing the transaction comparison fingerprint in a transaction comparison fingerprint cache table, and monitoring a frequency or number of times the CP transaction data matches a transaction comparison fingerprint; comparing the CP transaction data against at least one transaction comparison fingerprint in the transaction comparison fingerprint cache table to generate a comparison result; and based on the comparison result, or the monitored frequency or number of matches, generating the potential payment duplication alert.

In some examples, monitoring the flow of the CP transaction data across the plurality of communicatively-coupled CP transaction processing components includes monitoring for a failure or breakdown including at least one of a card decline, a network error, a request time out, a gateway time out, a failed response receipt, a bank error, a processor error, a lost connection, a power loss, a device reboot, or a device restart.

In some examples, the tenant in the multi-tenant network is an aesthetic medical practice in a network of medical service providers, and wherein the human user is a patient at the aesthetic medical practice.

In some examples, a non-transitory computer-readable storage medium is provided. The non-transitory computer-readable storage medium includes instructions that, when executed by a processing device, cause the processing device to perform operations summarized above, or described elsewhere herein.

Figure 17:
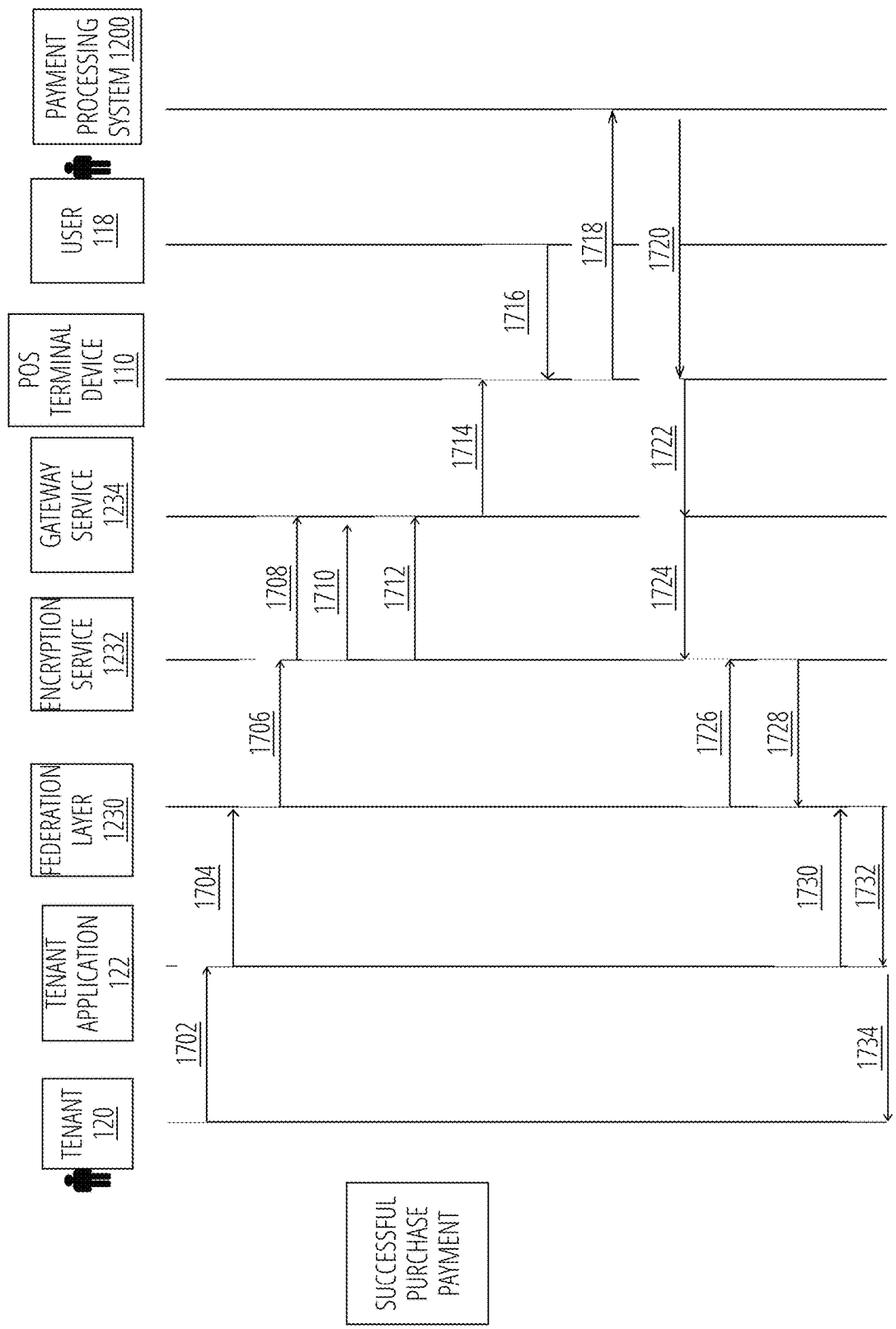
FIG. 17 illustrates an aspect of the subject matter in accordance with one embodiment.

FIG. 17 shows operations and communications in a successful flow of CP transaction data across a plurality of communicatively-coupled CP transaction processing components. The communicatively-coupled components include at least the POS terminal device 110 operating at a tenant 120 and invoked and controlled by a tenant application 122, a federation layer 1230 executing between tenants 120 in the multi-tenant network 1210 (or multi-tenant network 100), a peer-to-peer encryption service 1232 accessible by the POS terminal device 110 and invoked by a CP transaction request, a gateway service 1234 acting as an exclusive contact point for the POS terminal device 110, and an application-support server (for example, application server 104) executing or processing data for a payment application (e.g., the tenant application 122) to present at least some of the CP transaction data in a user interface of a mobile device (for example, user device 108) operated by the human user. The communicatively-coupled components cooperate and communicate with each other in a successful non-duplicated payment by a user 118 for a purchase of a subscription, item or service from a tenant 120.

At operation 1702, a staff member at the tenant 120 launches a tenant application 122 to invoke the POS terminal device 110. At operation 1704, the tenant application 122 communicates a charge including the transaction data for the relevant purchase of the subscription, item or service to the federation layer 1230. At operation 1706, the federation layer 1230 sends the transaction data using the encryption service 1232. At operation 1708, a check is made by the gateway service for a purchase duplication. This check may be made by or in conjunction with the communicatively-coupled payment processing system 1200. At operation 1710, a user signature is cached if there is no purchase duplication. At operation 1712, the encryption service 1232 sends a payment communication handshake to the gateway service 1234. At operation 1714, the gateway service 1234 sends a payment communication to the POS terminal device 110 and, in response thereto, in operation 1716 the user 118 swipes or taps a credit card at the POS terminal device 110 (i.e., the credit card is present) to instruct payment for the purchase of the subscription, item, or service from the tenant 120.

In operation 1718, the credit card payment information is sent from the POS terminal device 110 to the payment processing system 1200. In operation 1720, a response is received at the POS terminal device 110 from the payment processing system 1200 confirming a successful payment. In operation 1722, this payment confirmation and payment information is communicated to the gateway service 1234, and in operation 1724 is communicated back via the encryption service 1232. In operation 1726, the federation layer 1230 accesses a transaction status via the encryption service 1232. In operation 1728, the encryption service 1232 communicates the transaction status information to the federation layer 1230. In operation 1732, the federation layer 1230 communicates the transaction status information to the tenant application 122 and from there, in operation 1734, is rendered on a UI to the staff member at the tenant 120.

Figure 18:
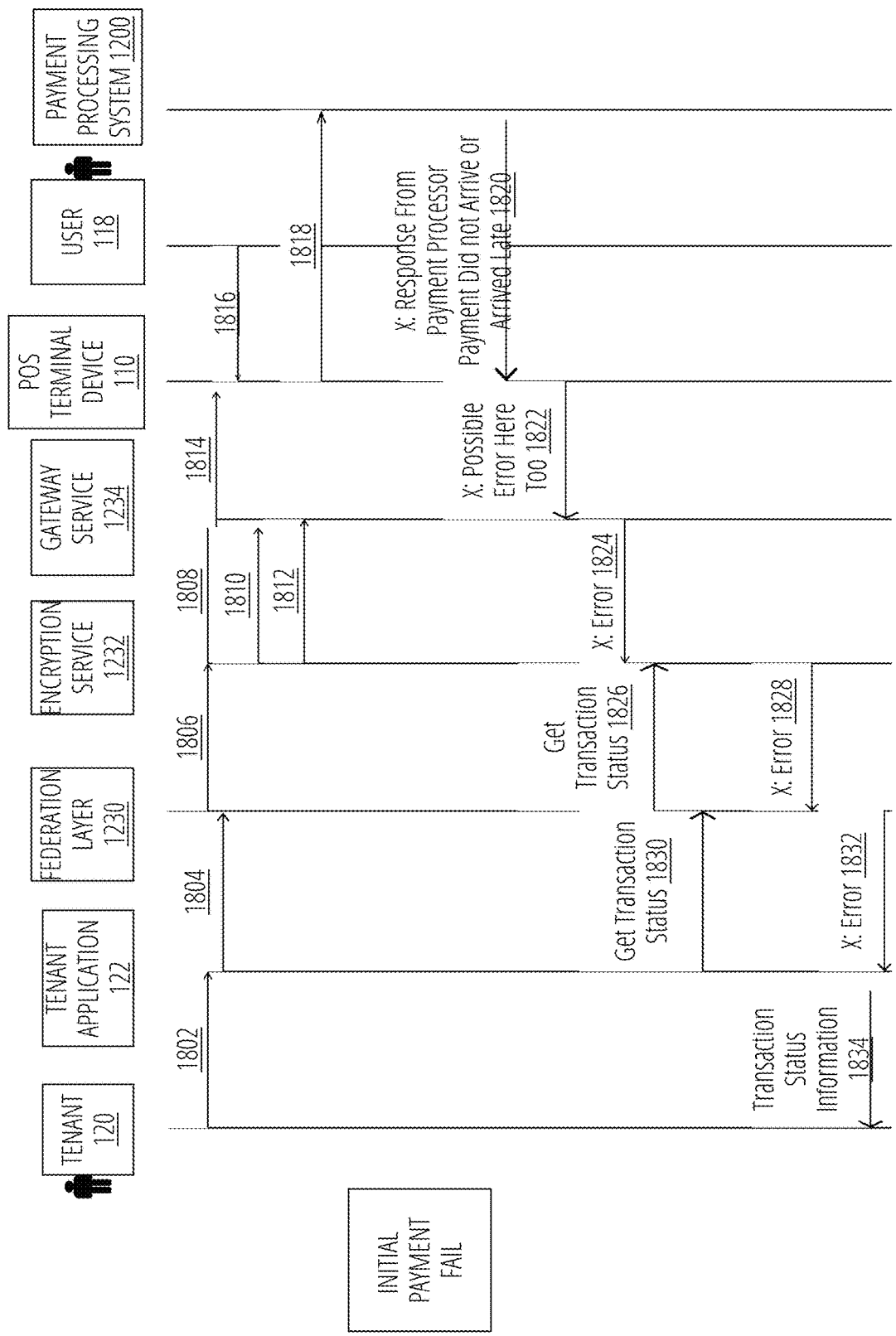
FIG. 18 illustrates an aspect of the subject matter in accordance with one embodiment.

FIG. 18 shows operations and communications across the plurality of communicatively-coupled CP transaction processing components for an initial payment attempt that failed.

As before, at operation 1802, a staff member at the tenant 120 launches a tenant application 122 to invoke the POS terminal device 110. At operation 1804, the tenant application 122 raises a charge including transaction data for the relevant purchase of the subscription, item or service to the federation layer 1230. At operation 1806, the federation layer 1230 sends the transaction data (pertaining to the charge) for encryption using the encryption service 1232. At operation 1808, a check is made by the gateway service 1234 for a purchase duplication. This check may be made by or in conjunction with the communicatively-coupled payment processing system 1200. At operation 1810, a user signature is cached if there is no purchase duplication. At operation 1812, the encryption service 1232 sends a payment communication handshake to the gateway service 1234. At operation 1814, the gateway service 1234 sends a payment communication to the POS terminal device 110 and, in response thereto, in operation 1816 the user 118 swipes or taps a credit card at the POS terminal device 110 (i.e., the credit card is present) to instruct payment for the purchase of the subscription, item, or service from the tenant 120. In operation 1818, the credit card payment information is sent from the POS terminal device 110 to the payment processing system 1200.

In this situation, however, in operation 1820, a response is received at the POS terminal device 110 from the payment processing system 1200 that a payment did not arrive or arrived late, i.e., outside a specified time. In operation 1822, a possible further error may occur too between the POS terminal device 110 and the gateway service 1234. Other errors are possible. As a result, in operation 1824 an error message is communicated via the encryption service 1232, as shown. In operation 1826, the federation layer 1230 accesses a transaction status via the encryption service 1232. In operation 1828, the encryption service 1232 communicates the error message information to the federation layer 1230. In operation 1830, the tenant application 122 accesses a transaction status at the federation layer 1230, and in operation 1832 the federation layer 1230 communicates the transaction status information (error message) to the tenant application 122. From there, in operation 1834, an alert is rendered on a UI to the staff member at the tenant 120.

Figure 19:
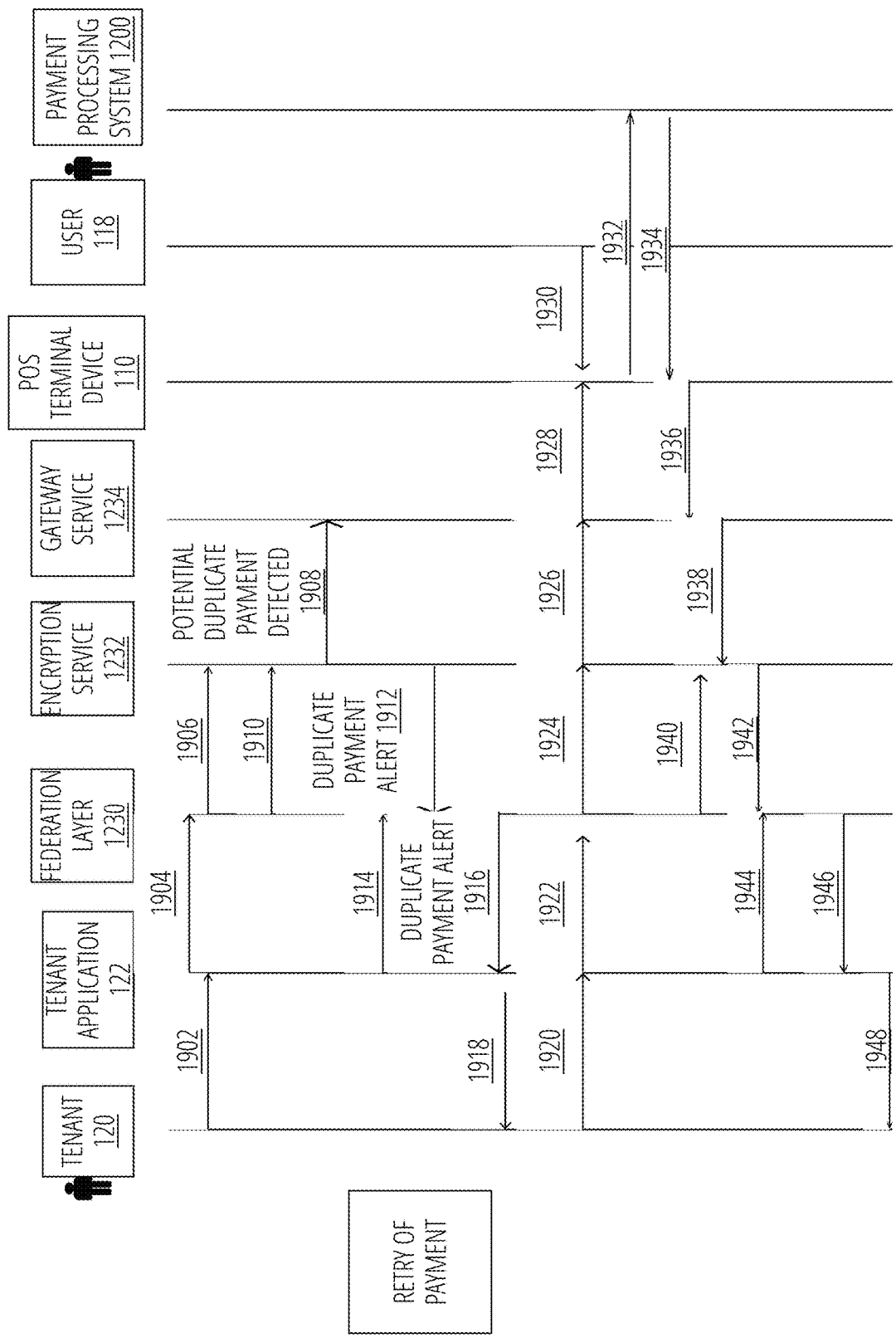
FIG. 19 illustrates an aspect of the subject matter in accordance with one embodiment.

FIG. 19 shows operations and communications of CP transaction data across a plurality of communicatively-coupled CP transaction processing components in a "retried" or duplicate payment by a user 118 for a purchase of a subscription, item or service from a tenant 120. As before, the communicatively-coupled components include those as described above.

At operation 1902, for the retried payment, a staff member at the tenant 120 launches a tenant application to invoke the POS terminal device 110. At operation 1904, the tenant application 122 again communicates a charge for the relevant purchase of the subscription, item or service to the federation layer 1230. At operation 1906 the purchase data is encrypted by the federation layer 1230 using the encryption service 1232. At operation 1908, a check is made by the gateway services 1234 for a purchase duplication. This check may be made by or in conjunction with the communicatively-coupled payment processing system 1200. A user signature is cached if there is no purchase duplication, but in this instance a duplicate payment attempt is detected. The payment duplication detection may be based on a transaction comparison fingerprint as described above. For example, a transaction comparison fingerprint may include or be triggered by a same tenant ID; a same user ID; a same user device 108; a same purchase amount; a same subscription, item, or service; a same POS terminal device 110, and/or a potential duplicate payment being detected within a certain configurable amount of time or qualifying period.

In response to receipt of a transaction status query in operation 1910, or by being autogenerated, a return message is communicated to the federation layer 1230 in operation 1912 including an alert indicating a potential duplicate payment has been detected. A similar transaction status request and alert may be exchanged between the tenant application 122 and the federation layer 1230 in operations 1914 and 1916. In operation 1918, the staff member is informed, via a UI display in the POS terminal device 110 operating at the tenant 120 and cooperating with the tenant application 122, that a potential duplicate payment has been detected. At this time, the staff member at the tenant 120 or the user 118 may, in light of the alert, elect not to proceed with the retried payment. The duplicate transaction terminates accordingly. No further attempts to pay are made.

If a payment is retried, in operation 1920, a staff member at the tenant 120 again launches a tenant application 122 (if needed to be launched again) to reinvoke the POS terminal device 110. At operation 1922, the tenant application 122 again communicates a charge (including the transaction data) for the relevant purchase of the subscription, item or service to the federation layer 1230. At operation 1924, the transaction data is encrypted using the encryption service 1232. This time, no check is made for a potential payment duplication. Instead, in operation 1926, the process proceeds directly to the encryption service 1232 sending a payment communication handshake to the gateway service 1234. At operation 1928, the gateway service 1234 sends a payment communication to the POS terminal device 110 and, in response thereto, in operation 1930, the user 118 swipes or taps a credit card at the POS terminal device 110 (i.e., the credit card is present) to instruct payment for the purchase of the subscription, item, or service from the tenant 120.

In operation 1932, the credit card payment information (including the transaction data) is sent from the POS terminal device 110 to the payment processing system 1200, or a third party payment processor if the payment processing system 1200 is offline or otherwise uncontactable. In operation 1934, a response is received at the POS terminal device 110 from the payment processing system 1200 (or third party) confirming a successful payment. In operation 1936, this payment confirmation and payment information is communicated to the gateway service 1234, and in operation 1938 is communicated back via the encryption service 1232. In operation 1940, the federation layer 1230 accesses a transaction status at the gateway service 1234 via the encryption service 1232. In operation 1942, the encryption service 1232 communicates the transaction status information to the federation layer 1230. In response to a query 1944, or automatically, the federation layer 1230 communicates in operation 1946 the transaction status information to the tenant application 122 and from there, in operation 1948, is rendered on a UI on the POS terminal device 110 to the staff member at the tenant 120.

Figure 20:
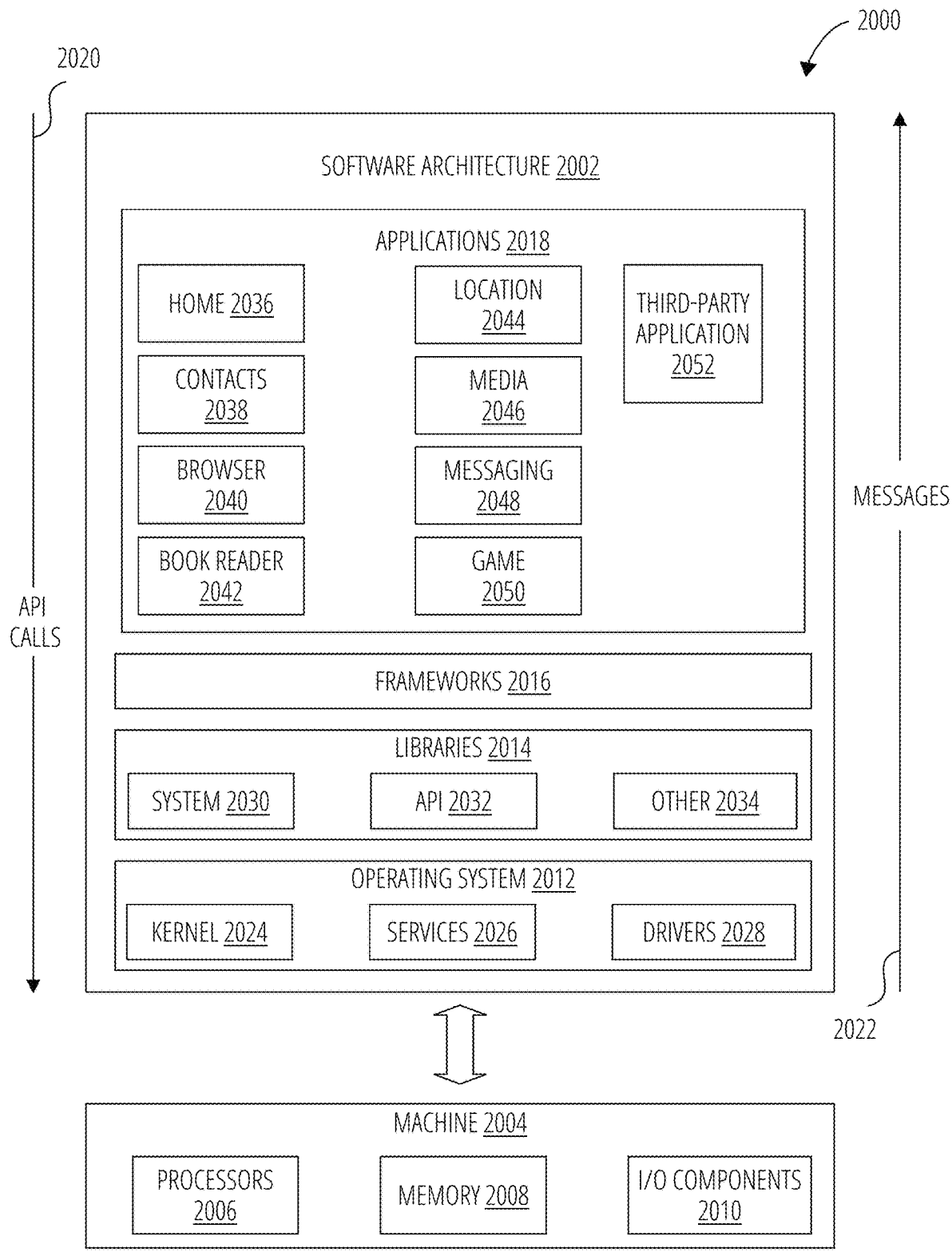
FIG. 20 illustrates a block diagram of a software architecture, according to some example embodiments.

FIG. 20 is a block diagram 2000 illustrating a software architecture 2002, which can be installed on any one or more of the devices herein. FIG. 20 is merely a non-limiting example of a software architecture, and it will be appreciated that many other architectures can be implemented to facilitate the functionality described herein. In various embodiments, the software architecture 2002 is implemented by hardware such as a machine 2004 of FIG. 20 that includes processors 2006, memory 2008, and I/O component 2010. In this example architecture, the software can be conceptualized as a stack of layers where each layer may provide particular functionality. For example, the software includes layers such as an operating system 2012, libraries 2014, frameworks 2016, and applications 2018. Operationally, the applications 2018 invoke application programming interface (API) calls (API calls) 2020 through the software stack and receive messages 2022 in response to the API calls 2020, consistent with some embodiments.

In various implementations, the operating system 2012 manages hardware resources and provides common services. The operating system 2012 includes, for example, a kernel 2024, services 2026, and drivers 2028. The kernel 2024 acts as an abstraction layer between the hardware and the other software layers, consistent with some embodiments. For example, the kernel 2024 provides memory management, processor management (e.g., scheduling), component management, networking, and security settings, among other functionality. The services 2026 can provide other common services for the other software layers. The drivers 2028 are responsible for controlling or interfacing with the underlying hardware, according to some embodiments. For instance, the drivers 2028 can include display drivers, camera drivers, BLUETOOTH® or BLUETOOTH® Low Energy drivers, flash memory drivers, serial communication drivers (e.g., Universal Serial Bus (USB) drivers), WI-FI® drivers, audio drivers, power management drivers, and so forth.

In some embodiments, the libraries 2014 provide a common low-level infrastructure utilized by the applications 2018. The libraries 2014 can include system libraries 2030 (e.g., C standard library) that can provide functions such as memory allocation functions, string manipulation functions, mathematic functions, and the like. In addition, the libraries 2014 can include API libraries 2032 such as media libraries (e.g., libraries to support presentation and manipulation of various media formats such as Moving Picture Experts Group-4 (MPEG4), Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or JPG), or Portable Network Graphics (PNG)), graphics libraries (e.g., an OpenGL framework used to render in two dimensions (2D) and three dimensions (3D) in a graphic content on a display), database libraries (e.g., SQLite to provide various relational database functions), web libraries (e.g., WebKit to provide web browsing functionality), and the like. The libraries 2014 can also include a wide variety of other libraries 2034 to provide many other APIs to the applications 2018.

The frameworks 2016 provide a common high-level infrastructure that can be utilized by the applications 2018, according to some embodiments. For example, the frameworks 2016 provide various graphical user interface (GUI) functions, high-level resource management, high-level location services, and so forth. The frameworks 2016 can provide a broad spectrum of other APIs that can be utilized by the applications 2018, some of which may be specific to a particular operating system or platform.

In an example embodiment, the applications 2018 include a home application 2036, a contacts application 2038, a browser application 2040, a book reader application 2042, a location application 2044, a media application 2046, a messaging application 2048, a game application 2050, and a broad assortment of other applications such as a third-party application 2052. According to some embodiments, the applications 2018 are programs that execute functions defined in the programs. Various programming languages can be employed to create one or more of the applications 2018, structured in a variety of manners, such as object-oriented programming languages (e.g., Objective-C, Java, or C++) or procedural programming languages (e.g., C or assembly language). In a specific example, the third-party application 2052 (e.g., an application developed using the ANDROID™ or IOS™ software development kit (SDK) by an entity other than the vendor of the particular platform) may be mobile software running on a mobile operating system such as IOS™, ANDROID™, WINDOWS® Phone, or another mobile operating system. In this example, the third-party application 2052 can invoke the API calls 2020 provided by the operating system 2012 to facilitate functionality described herein.

Figure 21:
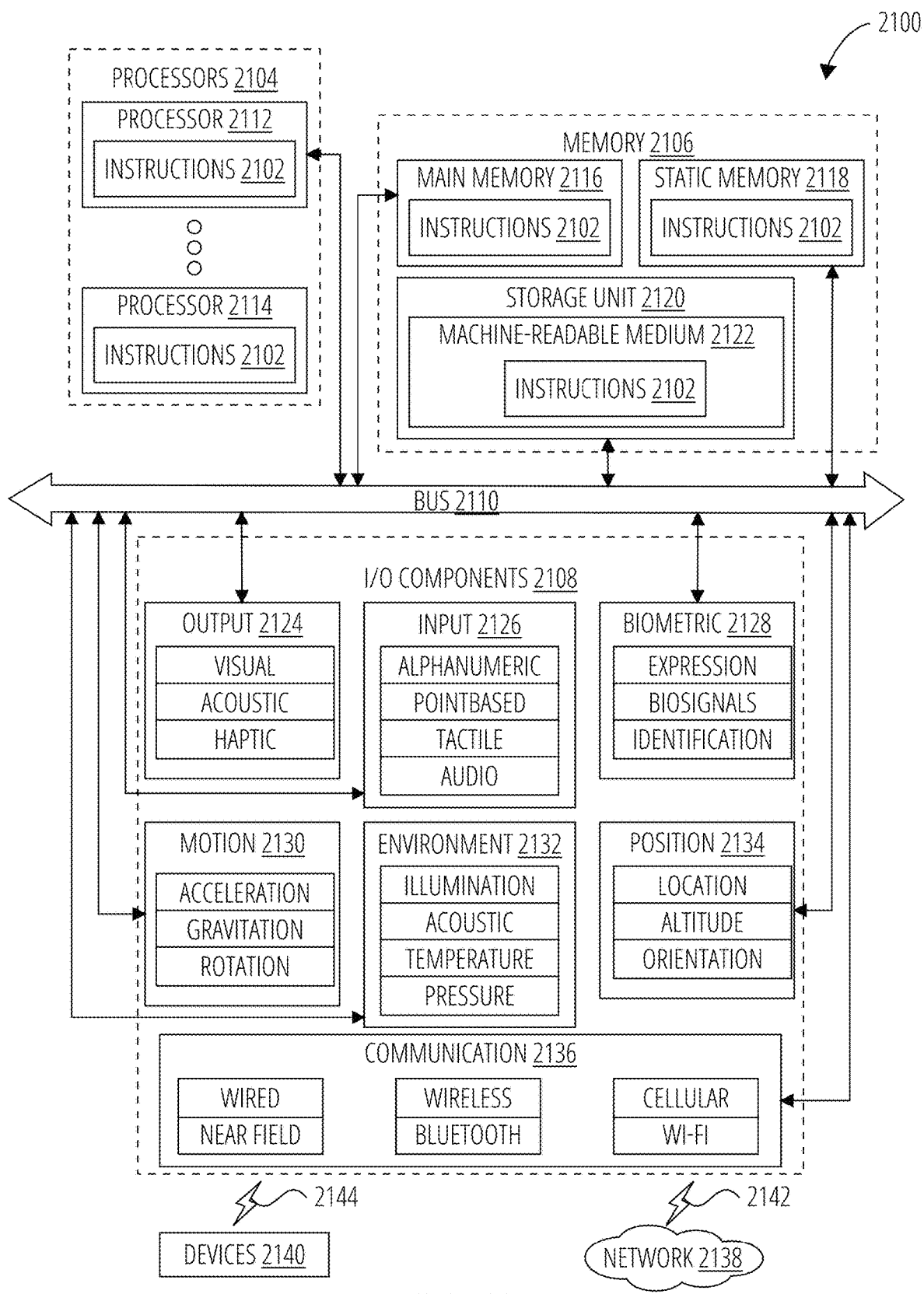
FIG. 21 illustrates a diagrammatic representation of a machine in the form of a computer system within which a set of instructions may be executed for causing the machine to perform any one or more of the methodologies discussed herein, according to an example embodiment.

FIG. 21 illustrates a diagrammatic representation of a machine 2100 in the form of a computer system within which a set of instructions may be executed for causing the machine to perform any one or more of the methodologies discussed herein, according to example embodiments. Specifically, FIG. 21 shows a diagrammatic representation of the machine 2100 in the example form of a computer system, within which instructions 2102 (e.g., software, a program, an application, an applet, an app, or other executable code) for causing the machine 2100 to perform any one or more of the methodologies discussed herein may be executed. The instructions 2102 transform the general, non-programmed machine 2100 into a particular machine 2100 programmed to carry out the described and illustrated functions in the manner described. In alternative embodiments, the machine 2100 operates as a standalone device or may be coupled (e.g., networked) to other machines. In a networked deployment, the machine 2100 may operate in the capacity of a server machine or a client machine in a server-client network environment, or as a peer machine in a peer-to-peer (or distributed) network environment. The machine 2100 may comprise, but not be limited to, a server computer, a client computer, a personal computer (PC), a tablet computer, a laptop computer, a netbook, a set-top box (STB), a PDA, an entertainment media system, a cellular telephone, a smartphone, a mobile device, a wearable device (e.g., a smartwatch), a smart home device (e.g., a smart appliance), other smart devices, a web appliance, a network router, a network switch, a network bridge, or any machine capable of executing the instructions 2102, sequentially or otherwise, that specify actions to be taken by the machine 2100. Further, while only a single machine 2100 is illustrated, the term "machine" shall also be taken to include a collection of machines 2100 that individually or jointly execute the instructions 2102 to perform any one or more of the methodologies discussed herein.

The 2100 may include processors 2104, memory 2106, and I/O components 2108, which may be configured to communicate with each other such as via a bus 2110. In an example embodiment, the processors 2104 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) may include, for example, a processor 2112 and a processor 2114 that may execute the instructions 2102. The term "processor" is intended to include multi-core processors that may comprise two or more independent processors (sometimes referred to as "cores") that may execute instructions contemporaneously. Although FIG. 21 shows multiple processors 2104, the machine 2100 may include a single processor with a single core, a single processor with multiple cores (e.g., a multi-core processor), multiple processors with a single core, multiple processors with multiples cores, or any combination thereof.

The memory 2106 may include a main memory 2116, a static memory 2118, and a storage unit 2120, both accessible to the processors 2104 such as via the bus 2110. The main memory 2116, the static memory 2118, and storage unit 2120 store the instructions 2102 embodying any one or more of the methodologies or functions described herein. The instructions 2102 may also reside, completely or partially, within the main memory 2116, within the static memory 2118, within machine-readable medium 2122 within the storage unit 2120, within at least one of the processors 2104 (e.g., within the processor's cache memory), or any suitable combination thereof, during execution thereof by the machine 2100.

The I/O components 2108 may include a wide variety of components to receive input, provide output, produce output, transmit information, exchange information, capture measurements, and so on. The specific I/O components 2108 that are included in a particular machine will depend on the type of machine. For example, portable machines such as mobile phones will likely include a touch input device or other such input mechanisms, while a headless server machine will likely not include such a touch input device. It will be appreciated that the I/O components 2108 may include many other components that are not shown in FIG. 21. The I/O components 2108 are grouped according to functionality merely for simplifying the following discussion, and the grouping is in no way limiting. In various example embodiments, the I/O components 2108 may include output components 2124 and input components 2126. The output components 2124 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 2126 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 2108 may include biometric components 2128, motion components 2130 environmental components 2132, or position components 2134, among a wide array of other components. For example, the biometric components 2128 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 2130 may include acceleration sensor components (e.g., accelerometer), gravitation sensor components, rotation sensor components (e.g., gyroscope), and so forth. The environmental components 2132 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 2134 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 2108 may include communication components 2136 operable to couple the machine 2100 to a network 2138 or devices 2140 via a coupling 2142 and a coupling 2144 respectively. For example, the communication components 2136 may include a network interface component or another suitable device to interface with the network 2138. In further examples, the communication components 2136 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 2140 may be another machine or any of a wide variety of peripheral devices (e.g., a peripheral device coupled via a USB).

Moreover, the communication components 2136 may detect identifiers or include components operable to detect identifiers. For example, the communication components 2136 may include Radio Frequency Identification (RFID) tag reader components, NFC smart tag detection components, optical reader components (e.g., an optical sensor to detect one-dimensional barcodes such as Universal Product Code (UPC) barcode, multi-dimensional bar codes such as Quick Response (QR) code, Aztec code, Data Matrix, Dataglyph, MaxiCode, PDF417, Ultra Code, UCC RSS-2D barcode, and other optical codes), or acoustic detection components (e.g., microphones to identify tagged audio signals). In addition, a variety of information may be derived via the communication components 2136, such as location via Internet Protocol (IP) geolocation, location via Wi-Fi® signal triangulation, location via detecting an NFC beacon signal that may indicate a particular location, and so forth.

The various memories (i.e., memory 2106, main memory 2116, static memory 2118, and/or memory of the processors 2104) and/or storage unit 2120 may store one or more sets of instructions and data structures (e.g., software) embodying or utilized by any one or more of the methodologies or functions described herein. These instructions (e.g., the instructions 2102), when executed by processor 2104, cause various operations to implement the disclosed embodiments.

As used herein, the terms "machine-storage medium," "device-storage medium," "computer-storage medium" mean the same thing and may be used interchangeably in this disclosure. The terms refer to a single or multiple storage devices and/or media (e.g., a centralized or distributed database, and/or associated caches and servers) that store executable instructions and/or data. The terms shall accordingly be taken to include, but not be limited to, solid-state memories, and optical and magnetic media, including memory internal or external to processors. Specific examples of machine-storage media, computer-storage media and/or device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks. The terms "machine-storage media," "computer-storage media," and "device-storage media" specifically exclude carrier waves, modulated data signals, and other such media, at least some of which are covered under the term "signal medium" discussed below.

In various example embodiments, one or more portions of the network 4320 may be an ad hoc network, an intranet, an extranet, a VPN, a LAN, a WLAN, a WAN, a WWAN, a MAN, the Internet, a portion of the Internet, a portion of the PSTN, a plain old telephone service (POTS) network, a cellular telephone network, a wireless network, a Wi-Fi® network, another type of network, or a combination of two or more such networks. For example, the network 2138 or a portion of the network 2138 may include a wireless or cellular network, and the coupling 2142 may be a Code Division Multiple Access (CDMA) connection, a Global System for Mobile communications (GSM) connection, or another type of cellular or wireless coupling. In this example, the coupling 2142 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long-range protocols, or other data transfer technology.

The instructions 2102 may be transmitted or received over the network 2138 using a transmission medium via a network interface device (e.g., a network interface component included in the communication components 2136) and utilizing any one of a number of well-known transfer protocols (e.g., hypertext transfer protocol (HTTP)). Similarly, the instructions 2102 may be transmitted or received using a transmission medium via the coupling 2144 (e.g., a peer-to-peer coupling) to the devices 2140. The terms "transmission medium" and "signal medium" mean the same thing and may be used interchangeably in this disclosure. The terms "transmission medium" and "signal medium" shall be taken to include any intangible medium that is capable of storing, encoding, or carrying the instructions 2102 for execution by the machine 2100, and includes digital or analog communications signals or other intangible media to facilitate communication of such software. Hence, the terms "transmission medium" and "signal medium" shall be taken to include any form of a modulated data signal, carrier wave, and so forth. The term "modulated data signal" means a signal that has one or more of its characteristics set or changed in such a matter as to encode information in the signal.

The terms "machine-readable medium," "computer-readable medium" and "device-readable medium" mean the same thing and may be used interchangeably in this disclosure. The terms are defined to include both machine-storage media and transmission media. Thus, the terms include both storage devices/media and carrier waves/modulated data signals.

What is claimed is:

1. A method comprising:
   detecting, by at least one hardware processor, a card-present (CP) transaction request that comprises a set of CP transaction data, the CP transaction request relating to a purchase of a subscription, item or service and initiated by a card swipe or card tap made by human user at a point-of-sale (POS) terminal device operating at a tenant in a multi-tenant network;
   accessing the CP transaction data;
   monitoring a flow of the CP transaction data across a plurality of communicatively-coupled CP transaction processing components, the CP transaction processing components including at least the POS terminal device, a federation layer executing between tenants in the multi-tenant network, a peer-to-peer encryption service accessible by the POS terminal device and invoked by the CP transaction request, a gateway service acting as an exclusive contact point for the POS terminal device, and an application-support device executing or processing data for a payment application to present at least some of the CP transaction data in a user interface of a mobile device operated by the human user;
   detecting a failure or breakdown in the flow of monitored CP transaction data;
   detecting an attempted re-initiation of the CP transaction request for a same purchase of the item or service, the attempted re-initiation of the CP transaction request made after the detected failure or breakdown in the flow of monitored CP transaction data, the re-initiated CP transaction request including re-initiated CP transaction data;
   accessing the re-initiated CP transaction data;
   based on the detected re-initiation of the CP transaction request, comparing, by the at least one hardware processor, the CP transaction data against the re-initiated CP transaction data to identify an attempted duplicated payment for the purchase of the item or service; and
   based on the identified attempted duplicated payment, initiating, by the at least one hardware processor, a payment deduplication phase by generating a potential payment duplication alert for presentation at the POS terminal device and/or in the user interface of the mobile device operated by the human user.

2. The method of claim 1, further comprising:
   based on a response to the payment duplication alert, progressing the payment deduplication phase by voiding, or facilitating a voiding of, either one of the initial and re-initiated CP transaction requests.

3. The method of claim 2, wherein progressing the payment deduplication phase further comprises processing a respective non-voided initial or re-initiated CP transaction request.

4. The method of claim 2, wherein the response to the potential payment deduplication alert is received at the POS terminal device.

5. The method of claim 2, wherein the response to the potential payment deduplication alert is received from the mobile device operated by the human user.

6. The method of claim 1, wherein comparing the CP transaction data against the re-initiated CP transaction data further comprises:
   inputting the CP transaction data into a machine-learned model trained to analyze a set of historical transaction data, the set of historical transaction data having been aggregated from one or more historical data sources, the one or more historical data sources including at least one microservice database collecting a particular aspect of transactional data processed by a corresponding microservice of the tenant in the multi-tenant network;

using an output of the machine-learned model to generate a transaction comparison fingerprint based on common or repeated tenant or human user payment transactions;

storing the transaction comparison fingerprint in a transaction comparison fingerprint cache table, and monitoring a frequency or number of times the CP transaction data matches a transaction comparison fingerprint;

comparing the CP transaction data against at least one transaction comparison fingerprint in the transaction comparison fingerprint cache table to generate a comparison result; and based on the comparison result, or the monitored frequency or number of matches, generating the potential payment duplication alert.

7. The method of claim 1, wherein monitoring the flow of the CP transaction data across the plurality of communicatively-coupled CP transaction processing components includes monitoring for a failure or breakdown including at least one of a card decline, a network error, a request time out, a gateway time out, a failed response receipt, a bank error, a processor error, a lost connection, a power loss, a device reboot, or a device restart.

8. The method of claim 1, wherein the tenant in the multi-tenant network is an aesthetic medical practice in a network of medical service providers, and wherein the human user is a patient at the aesthetic medical practice.

9. A payment processing system comprising:
at least one processor; and
a memory storing instructions that, when executed by the at least processor, cause the system to perform operations comprising:
detecting a card-present (CP) transaction request that comprises a set of CP transaction data, the CP transaction request relating to a purchase of an item or service and initiated by a card swipe or card tap made by human user at a point-of-sale (POS) terminal device operating at a tenant in a multi-tenant network;
accessing the CP transaction data;
monitoring a flow of the CP transaction data across a plurality of communicatively-coupled CP transaction processing components, the CP transaction processing components including at least the POS terminal device, a federation layer executing between tenants in the multi-tenant network, a peer-to-peer encryption service accessible by the POS terminal device and invoked by the CP transaction request, a gateway service acting as an exclusive contact point for the POS terminal device, and an application-support device executing or processing data for a payment application to present at least some of the CP transaction data in a user interface of a mobile device operated by the human user;
detecting a failure or breakdown in the flow of monitored CP transaction data;
detecting an attempted re-initiation of the CP transaction request for a same purchase of the item or service, the attempted re-initiation of the CP transaction request made after the detected failure or breakdown in the flow of monitored CP transaction data, the re-initiated CP transaction request including re-initiated CP transaction data;
accessing the re-initiated CP transaction data;
based on the detected re-initiation of the CP transaction request, comparing the CP transaction data against the re-initiated CP transaction data to identify an attempted duplicated payment for the purchase of the item or service; and based on the identified attempted duplicated payment, initiating a payment deduplication phase by generating a potential payment duplication alert for presentation at the POS terminal device and/or in the user interface of the mobile device operated by the human user.

10. The payment processing system of claim 9, wherein the operations further comprise:
based on a response to the payment duplication alert, progressing the payment deduplication phase by voiding, or facilitating a voiding of, either one of the initial and re-initiated CP transaction requests.

11. The payment processing system of claim 10, wherein progressing the payment deduplication phase further comprises processing a non-voided initial or re-initiated CP transaction request.

12. The payment processing system of claim 10, wherein the response to the potential payment deduplication alert is received at the POS terminal device.

13. The payment processing system of claim 10, wherein the response to the potential payment deduplication alert is received from the mobile device operated by the human user.

14. The payment processing system of claim 9, wherein comparing the CP transaction data against the re-initiated CP transaction data further comprises:
inputting the CP transaction data into a machine-learned model trained to analyze a set of historical transaction data, the set of historical transaction data having been aggregated from one or more historical data sources, the one or more historical data sources including at least one microservice database collecting a particular aspect of transactional data processed by a corresponding microservice of the tenant in the multi-tenant network;
using an output of the machine-learned model to generate a transaction comparison fingerprint based on common or repeated tenant or human user payment transactions;
storing the transaction comparison fingerprint in a transaction comparison fingerprint cache table, and monitoring a frequency or number of times the CP transaction data matches a transaction comparison fingerprint;
comparing the CP transaction data against at least one transaction comparison fingerprint in the transaction comparison fingerprint cache table to generate a comparison result; and
based on the comparison result, or the monitored frequency or number of matches, generating the potential payment duplication alert.

15. The payment processing system of claim 9, wherein monitoring the flow of the CP transaction data across the plurality of communicatively-coupled CP transaction process components includes monitoring for a failure or breakdown including at least one of a card decline, a network error, a request time out, a gateway time out, a failed response receipt, a bank error, a processor error, a lost connection, a power loss, a device reboot, and a device restart.

16. The payment processing system of claim 9, wherein the tenant in the multi-tenant network is an aesthetic medical practice in a network of medical service providers, and wherein the human user is a patient at the aesthetic medical practice.

17. A non-transitory computer-readable storage medium, the non-transitory computer-readable storage medium including instructions that when executed by a processing device, cause the processing device to perform operations comprising:

detecting, by at least one hardware processor, a card-present (CP) transaction request that comprises a set of CP transaction data, the CP transaction request relating to a purchase of an item or service and initiated by a card swipe or card tap made by human user at a point-of-sale (POS) terminal device operating at a tenant in a multi-tenant network;

accessing the CP transaction data;

monitoring a flow of the CP transaction data across a plurality of communicatively-coupled CP transaction processing components, the CP transaction processing components including at least the POS terminal device, a federation layer executing between tenants in the multi-tenant network, a peer-to-peer encryption service accessible by the POS terminal device and invoked by the CP transaction request, a gateway service acting as an exclusive contact point for the POS terminal device, and an application-support device executing or processing data for a payment application to present at least some of the CP transaction data in a user interface of a mobile device operated by the human user;

detecting a failure or breakdown in the flow of monitored CP transaction data;

detecting an attempted re-initiation of the CP transaction request for a same purchase of the item or service, the attempted re-initiation of the CP transaction request made after the detected failure or breakdown in the flow of monitored CP transaction data, the re-initiated CP transaction request including re-initiated CP transaction data;

accessing the re-initiated CP transaction data;

based on the detected re-initiation of the CP transaction request, comparing, by the at least one hardware processor, the CP transaction data against the re-initiated CP transaction data to identify an attempted duplicated payment for the purchase of the item or service; and based on the identified attempted duplicated payment, initiating, by the at least one hardware processor, a payment deduplication phase by generating a potential payment duplication alert for presentation at the POS terminal device and/or in the user interface of the mobile device operated by the human user.

18. The non-transitory computer-readable storage medium of claim 17, wherein the operations further comprise:

based on a response to the payment duplication alert, progressing the payment deduplication phase by voiding, or facilitating a voiding of, either one of the initial and re-initiated CP transaction requests.

19. The non-transitory computer-readable storage medium of claim 18, wherein progressing the payment deduplication phase further comprises processing a non-voided initial or re-initiated CP transaction request.

20. The non-transitory computer-readable storage medium of claim 18, wherein the response to the potential payment deduplication alert is received at the POS terminal device.

21. The non-transitory computer-readable storage medium of claim 18, wherein the response to the potential payment deduplication alert is received from the mobile device operated by the human user.

22. The non-transitory computer-readable storage medium of claim 17, wherein comparing the CP transaction data against the re-initiated CP transaction data further comprises:

inputting the CP transaction data into a machine-learned model trained to analyze a set of historical transaction data, the set of historical transaction data having been aggregated from one or more historical data sources, the one or more historical data sources including at least one microservice database collecting a particular aspect of transactional data processed by a corresponding microservice of the tenant in the multi-tenant network;

using an output of the machine-learned model to generate a transaction comparison fingerprint based on common or repeated tenant or human user payment transactions;

storing the transaction comparison fingerprint in a transaction comparison fingerprint cache table, and monitoring a frequency or number of times the CP transaction data matches a transaction comparison fingerprint;

comparing the CP transaction data against at least one transaction comparison fingerprint in the transaction comparison fingerprint cache table to generate a comparison result; and based on the comparison result, or the monitored frequency or number of matches, generating the potential payment duplication alert.

23. The non-transitory computer-readable storage medium of claim 17, wherein monitoring the flow of the CP transaction data across the plurality of communicatively-coupled CP transaction process components includes monitoring for a failure or breakdown including at least one of a card decline, a network error, a request time out, a gateway time out, a failed response receipt, a bank error, a processor error, a lost connection, a power loss, a device reboot, and a device restart.

24. The non-transitory computer-readable storage medium of claim 17, wherein the tenant in the multi-tenant network is an aesthetic medical practice in a network of medical service providers, and wherein the human user is a patient at the aesthetic medical practice.

* * * * *